(12) United States Patent
Kanayama et al.

(10) Patent No.: US 8,221,754 B2
(45) Date of Patent: Jul. 17, 2012

(54) ANTIHUMAN α9 INTEGRIN ANTIBODY AND USE OF THE SAME

(75) Inventors: Masashi Kanayama, Sapporo (JP); Daisuke Kurotaki, Sapporo (JP); Shigeyuki Kon, Sapporo (JP); Toshimitsu Uede, Sapporo (JP)

(73) Assignee: Gene Techno Science Co., Ltd., Sapporo-shi (JP)

( * ) Notice: Subject to any disclaimer, the term of this patent is extended or adjusted under 35 U.S.C. 154(b) by 424 days.

(21) Appl. No.: 12/309,001

(22) PCT Filed: Jul. 11, 2007

(86) PCT No.: PCT/JP2007/064129
§ 371 (c)(1),
(2), (4) Date: Dec. 31, 2008

(87) PCT Pub. No.: WO2008/007804
PCT Pub. Date: Jan. 17, 2008

(65) Prior Publication Data
US 2009/0252734 A1    Oct. 8, 2009

(30) Foreign Application Priority Data
Jul. 12, 2006 (JP) .................... 2006-191836

(51) Int. Cl.
*A61K 39/395* (2006.01)
*A61P 35/00* (2006.01)
*C07K 16/18* (2006.01)

(52) U.S. Cl. .................... 424/139.1; 530/387.9
(58) Field of Classification Search ............... 424/139.1; 530/387.9
See application file for complete search history.

(56) References Cited

U.S. PATENT DOCUMENTS

| 7,595,045 B2 * | 9/2009 | Kurotaki et al. ............ 424/130.1 |
| 2008/0152653 A1 | 6/2008 | Kurotaki et al. |
| 2010/0329980 A1 * | 12/2010 | Kumar et al. ................. 424/9.1 |

FOREIGN PATENT DOCUMENTS

| EP | 0 917 878 A1 | | 5/1999 |
| WO | 99/06391 | | 2/1999 |
| WO | WO 2004/003019 | * | 6/2004 |
| WO | 2006/075784 | | 7/2006 |

OTHER PUBLICATIONS

MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Seaver (Genetic Engineering 14(14):pp. 10 and 21 (1994)).*
Suntharalingam et al. (NEJM 355:1018-1029 (2006)).*
Flieschmann et al. (Expert. Opin. Drug Safety 3(5):391-403 (2004)).*
Orbach et al. (Clinical Rev. Allergy Immunol. 29(3):173-184 (2005).*
Search Report in respect of counterpart EP Application No. 07768434.5.
Taooka, Y., et al., "The Integrin α9β1 Mediates Adhesion to Activated Endothelial Cells and Transendothelial Neutrophil Migration through Interaction with Vascular Cell Adhesion Molecule-1", *The Journal of Cell Biology*, 1999, vol. 145, No. 2, pp. 413-420.
Basora, N., et al., "Expression of the α9β1 Integrin in Human Colonic Epithelial Cells: Resurgence of the Fetal Phenotype in a Subset of Colon Cancers and Adenocarcinoma Cell Lines", *International Journal of Cancer*, 1998, vol. 75, No. 5, pp. 738-743.
Hibi, K., et al., "Aberrant unpregulation of a novel integrin α subunit gene at 3p21.3 in small cell lung cancer", *Oncogene*, 1994, vol. 9, No. 2, pp. 611-619.
Smith, L. L., et al. "Osteopontin N-terminal domain contains a cryptic adhesive sequence recognized by alpha9beta1 integrin." *The Journal of Biological Chemistry* (1996) vol. 271, No. 45, pp. 28485-28491.

* cited by examiner

*Primary Examiner* — Lynn Bristol
(74) *Attorney, Agent, or Firm* — Ladas & Parry LLP

(57) ABSTRACT

The present invention relates to: an antibody, particularly a monoclonal antibody, a chimeric antibody, a humanized antibody and a human antibody, which specifically recognize human α9 integrin; a hybridoma cell which produces the monoclonal antibody; a method for producing the monoclonal antibody; a method for producing the hybridoma cell; a therapeutic agent comprising the anti-human α9 integrin antibody; a diagnostic agent comprising the human α9 integrin antibody; and a method for screening a compound which inhibits the activity of human α9 integrin.

10 Claims, 10 Drawing Sheets

Fig. 1-1

Anti-human α9 integrin antibody Heavy chain CDR

```
                            CDRH1                                                    CDRH2
SEQ ID NO:50 1K11(H)   1:VQLQESGPELVKPGASVKIPCKASGYTFT D-YNMD WVKQSHGKSLEWIG DINPNNGGTIY  59
SEQ ID NO:51 21C5(H)   1:VQLQESGGGLVKPGGSLKLSCAASGFTFS D-YYMY WVRQTPEKRLEWVA TISDGGNYT-Y  58
SEQ ID NO:52 24I11(H)  1:VKLQESGAELVKPGASVKLSCTASGFNIK DTY-VH WVKQRPEQGLEWIG NIDPANGNTKY  59
SEQ ID NO:53 25B6(H)   1:VKLQQSGPGLVAPSQSLSITCTVSGFSLI S-YGVH MWVRQPPGKGLEWLG VIWSGGSTN-Y   58
SEQ ID NO:54 28S1(H)   1:VKLQESGPGLVAPSQSLSITCTVSGFSLI GYGVN-MWVRQPPGKGLEWLG MIWGDGI-TEY   58

1K11(H)    60:NQKFQG-KATLTVDKSSSTAYMELRSLTSEDTAVYYCAR--SGVIST----DY WGQGTTV  112
21C5(H)    59:YPDSVKGRFTISRDNAKNNLYLQMSSLKSEDTAMYYCAR DRDGSSL----FAY WGQGTTV  114
24I11(H)   60:DPKFQG-KATITADTSSNTAYLHLSSLTSEDTAVYYCAR WLRHF----YYAMDY WGQGTTV  115
25B6(H)    59:NSALM-SRLSISKDNFKSQVFLKMNSLQTDDTAIYYCAR DYGNYPW----FAY WGQGTTV   113
28S1(H)    59:NSALKSRLSISKDNSKSQVFLKMN-SLQTDDTARYYCAR DASSGYG----FAY WGQGTTV   113

1K11(H)    113:TVSS  116
21C5(H)    115:TVSS  118
24I11(H)   116:TVSS  119
25B6(H)    114:TVS-  116
28S1(H)    114:TVSS  117
```

Fig. 1-2

Anti-human α9 integrin antibody Light chain CDR

|  |  |  | CDRL1 | | CDRL2 | |
|---|---|---|---|---|---|---|
| SEQ ID NO:55 | 1K11(L) | 1: | DIQMTQSPPSLSASLGERVSLTQ | RASQEISGYLI----WLQQKPDGTIQRLIY | AASTLDS | 55 |
| SEQ ID NO:56 | 21C5(L) | 1: | HPDDTVSKFMST-SVGDRVSITQ | KASQDVNIAVA----WYQQRPGQSPKLLIY | WASTRHT | 55 |
| SEQ ID NO:57 | 24I11(L) | 1: | DIQMTQSPASLAASVGETVTITQ | RASENIYYSLA----WYQQKQGKSPQLLIY | NANSLED | 56 |
| SEQ ID NO:58 | 25B6(L) | 1: | HPDDTVSKFMST-SVGDRVSITQ | KASQDVNTAVA----WYQQKPGQSPKLLIY | SASYRYT | 55 |
| SEQ ID NO:59 | 28S1(L) | 1: | YIVLTQSPAIMSASLGERVTMTQ | TASSSVSSSYL----HWYQQKPGSSPKLWIY | STNLAS | 57 |

|  |  | | CDRL3 | |
|---|---|---|---|---|
| 1K11(L) | 56: | GVPKRFSGSRSGSDYSLTISSLESEDFADYYCLQ-YANYPPT FGGGTKLEIKR | 107 |
| 21C5(L) | 56: | GVPDRFTGSGSGTDYTLTISSVQAEDLALYYCQQ-HYNT-PWT FGGGTKLEIKR | 107 |
| 24I11(L) | 57: | GVPSRFSGSGSGTQYSMKINSMQPEDTATYFCKQ AYD-VPYT FGGGTKLELKR | 108 |
| 25B6(L) | 56: | GVPDRFTGSGSGTDFTFTISSVQAEDLAVYYCQQ HYST-PCA FGGGTKLEIKR | 107 |
| 28S1(L) | 58: | GVPARFSGSGSGTSYSLTISSMEAEDAATYYCHQ-YHRSPYT FGGGTKLEIKR | 109 |

Fig. 5
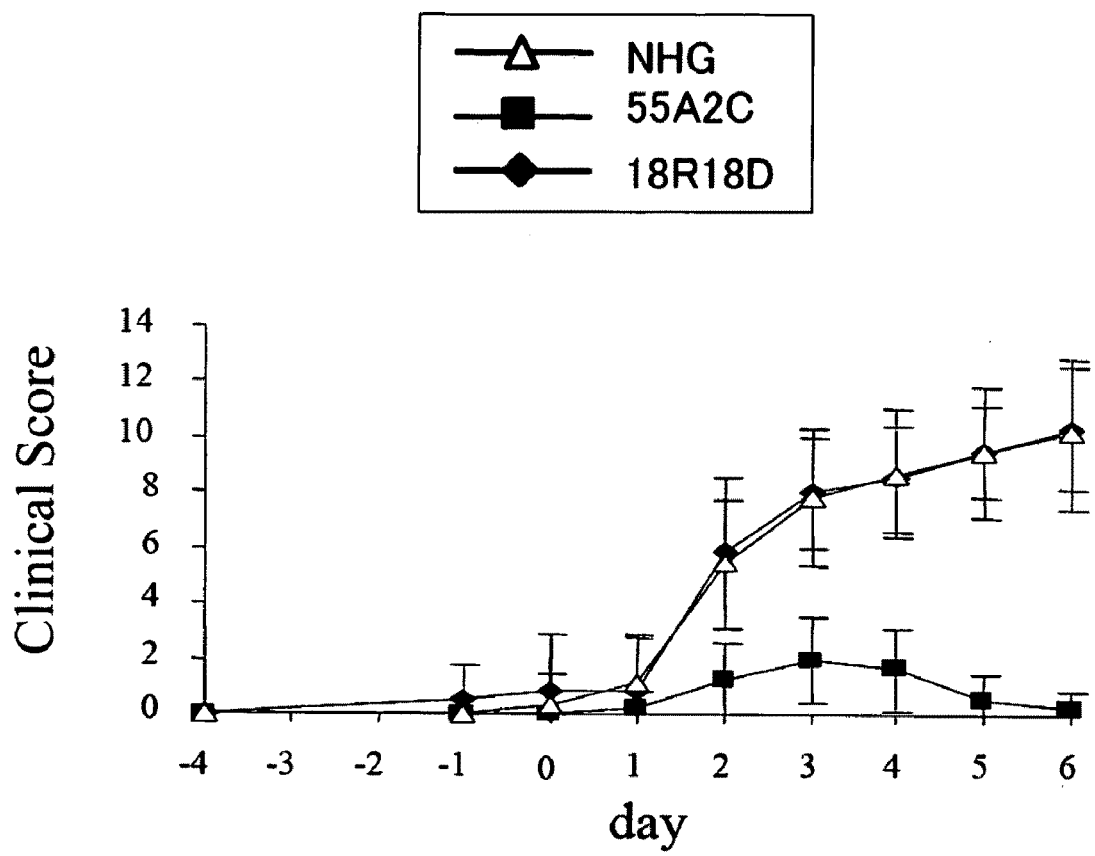
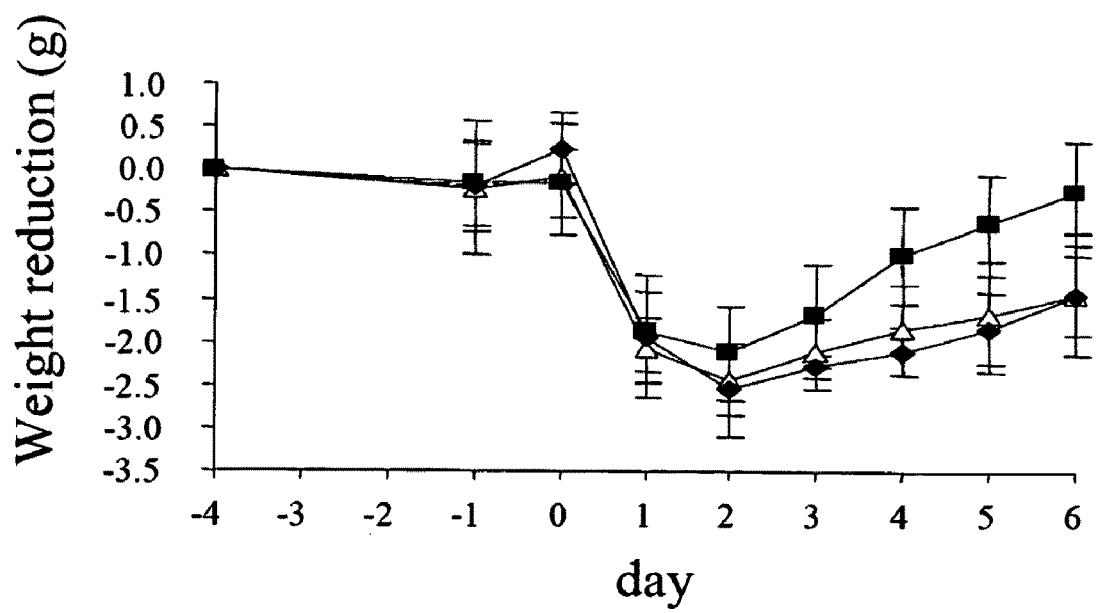

Fig. 7
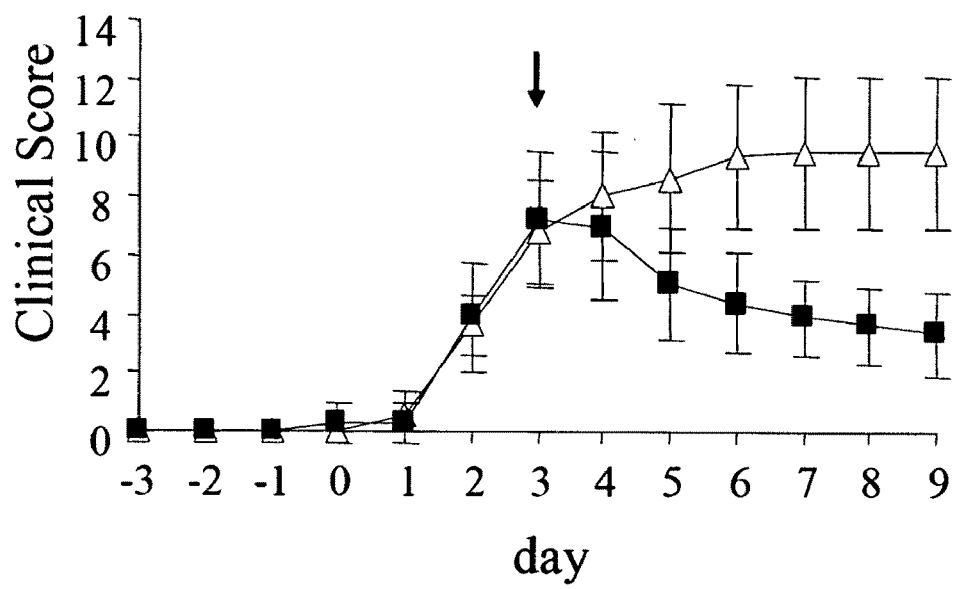
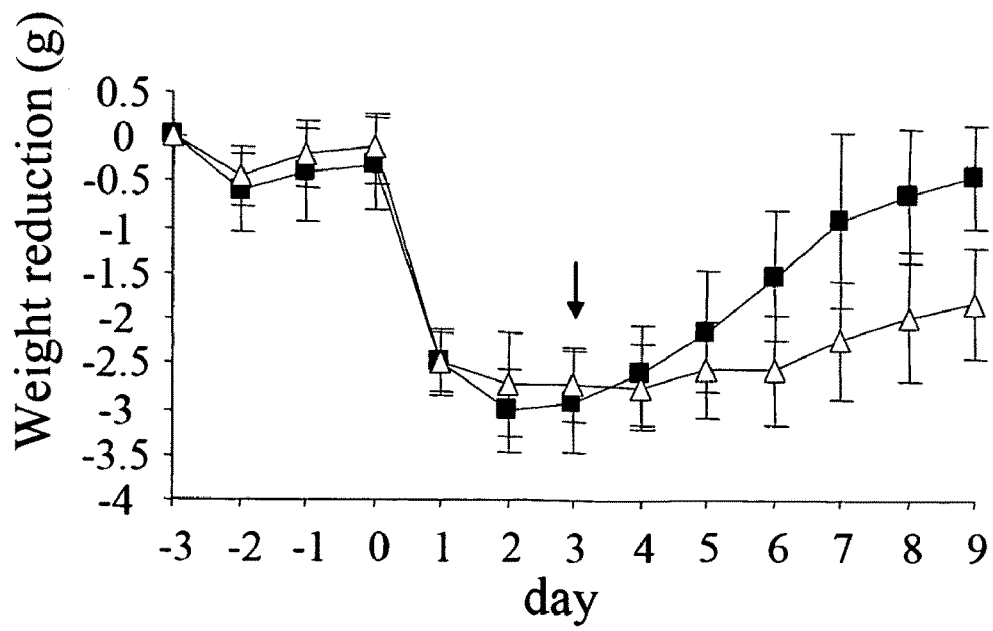

Fig. 9
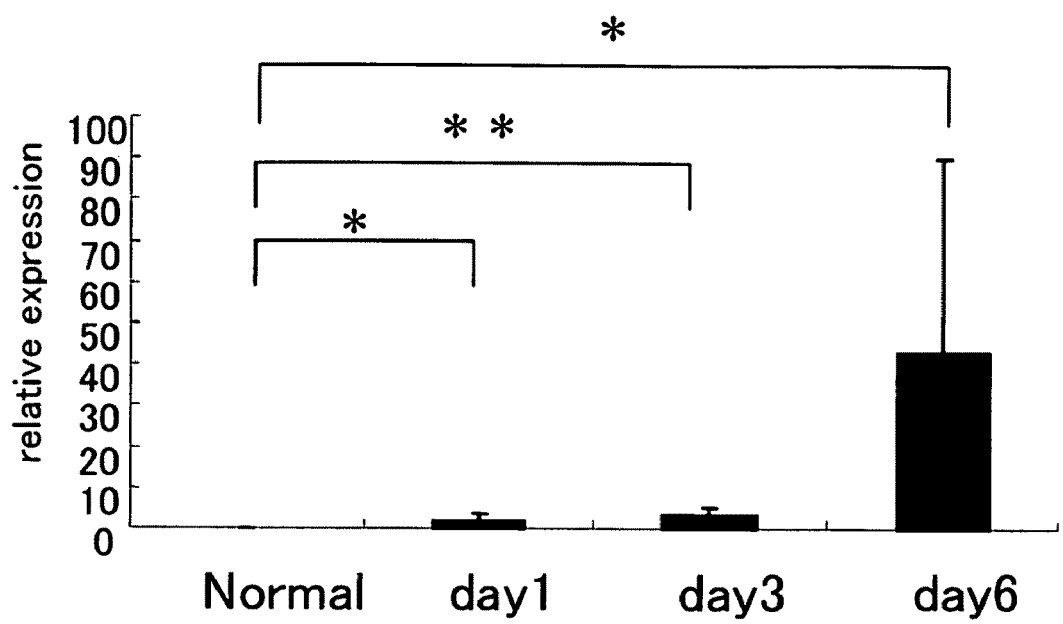
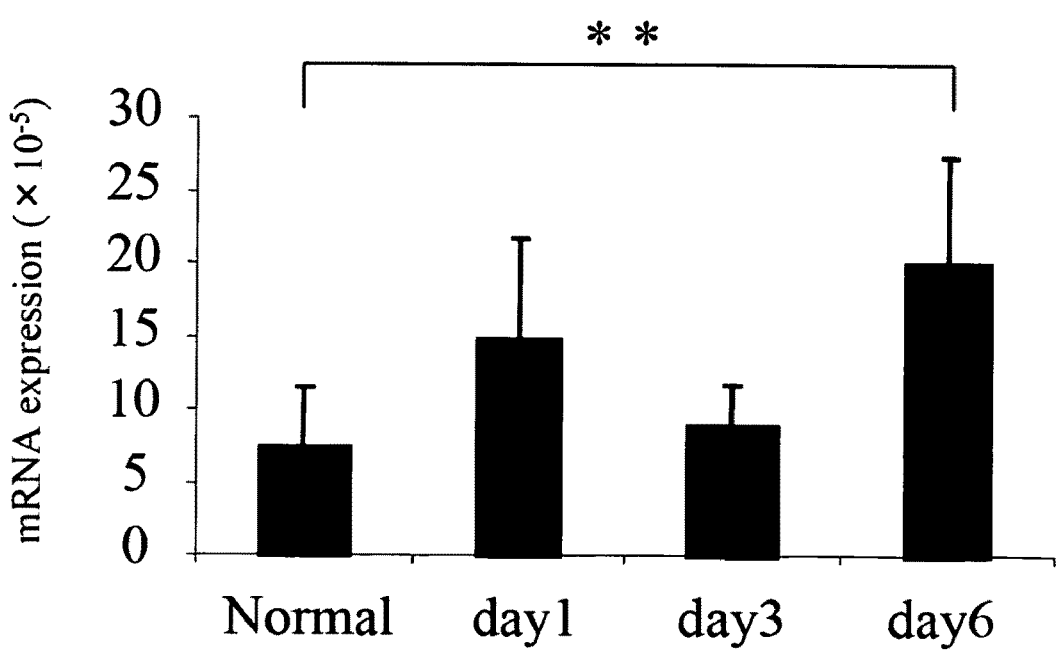

SEQUENCE LISTING

<160> NUMBER OF SEQ ID NOS: 59

<210> SEQ ID NO 1
<211> LENGTH: 12
<212> TYPE: PRT
<213> ORGANISM: Homo sapiens

<400> SEQUENCE: 1

Phe Gln Gly Pro Ala Asp Ser Phe Phe Gly Tyr Ala
1               5                   10

<210> SEQ ID NO 2
<211> LENGTH: 18
<212> TYPE: PRT
<213> ORGANISM: Homo sapiens

<400> SEQUENCE: 2

Lys Ser Pro Gly Ala Val Phe Lys Cys Arg Val His Thr Asn Pro Asp
1               5                   10                  15

Arg Arg

<210> SEQ ID NO 3
<211> LENGTH: 18
<212> TYPE: PRT
<213> ORGANISM: Homo sapiens

<400> SEQUENCE: 3

Trp Met Gly Val Ser Leu Ala Arg Gln Pro Lys Ala Asp Gly Arg Val
1               5                   10                  15

Leu Ala

<210> SEQ ID NO 4
<211> LENGTH: 15
<212> TYPE: PRT
<213> ORGANISM: Homo sapiens

<400> SEQUENCE: 4

Cys Ala His Arg Trp Lys Asn Ile Tyr Tyr Glu Ala Asp His Ile
1               5                   10                  15

<210> SEQ ID NO 5
<211> LENGTH: 18
<212> TYPE: PRT
<213> ORGANISM: Homo sapiens

<400> SEQUENCE: 5

Gly Phe Cys Tyr Ile Ile Pro Ser Asn Leu Gln Ala Lys Gly Arg Thr
1               5                   10                  15

Leu Ile

<210> SEQ ID NO 6
<211> LENGTH: 18
<212> TYPE: PRT
<213> ORGANISM: Homo sapiens

<400> SEQUENCE: 6

Val Met Gly Ala Pro Gly Ser Phe Tyr Trp Ala Gly Thr Ile Lys Val
1               5                   10                  15

Leu Asn

<210> SEQ ID NO 7

```
<211> LENGTH: 15
<212> TYPE: PRT
<213> ORGANISM: Homo sapiens

<400> SEQUENCE: 7

Val Ile Met Asn Arg Arg Tyr Thr Tyr Leu Gly Tyr Ala Val Thr
1               5                   10                  15

<210> SEQ ID NO 8
<211> LENGTH: 18
<212> TYPE: PRT
<213> ORGANISM: Homo sapiens

<400> SEQUENCE: 8

Val Tyr Ile Phe Arg Ala Asp Arg Arg Ser Gly Thr Leu Ile Lys Ile
1               5                   10                  15

Phe Gln

<210> SEQ ID NO 9
<211> LENGTH: 24
<212> TYPE: PRT
<213> ORGANISM: Homo sapiens

<400> SEQUENCE: 9

Gln Tyr Ser Met Lys Leu Ser Gly Gln Lys Ile Asn Pro Val Leu Arg
1               5                   10                  15

Met Phe Gly Gln Ser Ile Ser Gly
            20

<210> SEQ ID NO 10
<211> LENGTH: 18
<212> TYPE: PRT
<213> ORGANISM: Homo sapiens

<400> SEQUENCE: 10

Val Val Leu Leu Arg Ala Arg Pro Val Ile Thr Val Asp Val Ser Ile
1               5                   10                  15

Phe Leu

<210> SEQ ID NO 11
<211> LENGTH: 18
<212> TYPE: PRT
<213> ORGANISM: Homo sapiens

<400> SEQUENCE: 11

Arg His Tyr Val Ala His Val Lys Arg Arg Val Gln Asp Val Ile Ser
1               5                   10                  15

Pro Ile

<210> SEQ ID NO 12
<211> LENGTH: 30
<212> TYPE: PRT
<213> ORGANISM: Homo sapiens

<400> SEQUENCE: 12

Glu Leu Pro Pro Leu Thr Pro Val Leu Arg Trp Lys Lys Gly Gln Lys
1               5                   10                  15

Ile Ala Gln Lys Asn Gln Thr Val Phe Glu Arg Asn Cys Arg
            20                  25                  30

<210> SEQ ID NO 13
<211> LENGTH: 12
<212> TYPE: PRT
```

<213> ORGANISM: Homo sapiens

<400> SEQUENCE: 13

Tyr Leu Ala Leu Gly Ala Val Lys Asn Ile Ser Leu
1               5                   10

<210> SEQ ID NO 14
<211> LENGTH: 18
<212> TYPE: PRT
<213> ORGANISM: Homo sapiens

<400> SEQUENCE: 14

Cys Ser Val Gly Phe Pro Phe Met Arg Ser Lys Ser Lys Tyr Glu Phe
1               5                   10                  15

Ser Val

<210> SEQ ID NO 15
<211> LENGTH: 21
<212> TYPE: PRT
<213> ORGANISM: Homo sapiens

<400> SEQUENCE: 15

Ser Ser Ser Val Ile Gln Phe Met Ser Arg Ala Lys Val Lys Val Asp
1               5                   10                  15

Pro Ala Leu Arg Val
            20

<210> SEQ ID NO 16
<211> LENGTH: 5
<212> TYPE: PRT
<213> ORGANISM: Homo sapiens

<400> SEQUENCE: 16

Asp Tyr Asn Met Asp
1               5

<210> SEQ ID NO 17
<211> LENGTH: 5
<212> TYPE: PRT
<213> ORGANISM: Homo sapiens

<400> SEQUENCE: 17

Asp Tyr Tyr Met Tyr
1               5

<210> SEQ ID NO 18
<211> LENGTH: 5
<212> TYPE: PRT
<213> ORGANISM: Homo sapiens

<400> SEQUENCE: 18

Asp Thr Tyr Val His
1               5

<210> SEQ ID NO 19
<211> LENGTH: 5
<212> TYPE: PRT
<213> ORGANISM: Homo sapiens

<400> SEQUENCE: 19

Ser Tyr Gly Val His
1               5

<210> SEQ ID NO 20

```
<211> LENGTH: 17
<212> TYPE: PRT
<213> ORGANISM: Homo sapiens

<400> SEQUENCE: 20

Asp Ile Asn Pro Asn Asn Gly Gly Thr Ile Tyr Asn Gln Lys Phe Gln
1               5                   10                  15

Gly

<210> SEQ ID NO 21
<211> LENGTH: 17
<212> TYPE: PRT
<213> ORGANISM: Homo sapiens

<400> SEQUENCE: 21

Thr Ile Ser Asp Gly Gly Asn Tyr Thr Tyr Tyr Pro Asp Ser Val Lys
1               5                   10                  15

Gly

<210> SEQ ID NO 22
<211> LENGTH: 17
<212> TYPE: PRT
<213> ORGANISM: Homo sapiens

<400> SEQUENCE: 22

Asn Ile Asp Pro Ala Asn Gly Asn Thr Lys Tyr Asp Pro Lys Phe Gln
1               5                   10                  15

Gly

<210> SEQ ID NO 23
<211> LENGTH: 16
<212> TYPE: PRT
<213> ORGANISM: Homo sapiens

<400> SEQUENCE: 23

Val Ile Trp Ser Gly Gly Ser Thr Asn Tyr Asn Ser Ala Leu Met Ser
1               5                   10                  15

<210> SEQ ID NO 24
<211> LENGTH: 8
<212> TYPE: PRT
<213> ORGANISM: Homo sapiens

<400> SEQUENCE: 24

Ser Gly Val Ile Ser Thr Asp Tyr
1               5

<210> SEQ ID NO 25
<211> LENGTH: 10
<212> TYPE: PRT
<213> ORGANISM: Homo sapiens

<400> SEQUENCE: 25

Asp Arg Asp Gly Ser Ser Leu Phe Ala Tyr
1               5                   10

<210> SEQ ID NO 26
<211> LENGTH: 11
<212> TYPE: PRT
<213> ORGANISM: Homo sapiens

<400> SEQUENCE: 26

Trp Leu Arg His Phe Tyr Tyr Ala Met Asp Tyr
1               5                   10
```

<210> SEQ ID NO 27
<211> LENGTH: 10
<212> TYPE: PRT
<213> ORGANISM: Homo sapiens

<400> SEQUENCE: 27

Asp Tyr Gly Asn Tyr Pro Trp Phe Ala Tyr
1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Glu Ile Ser Gly Tyr Leu Ile
1               5                   10

<210> SEQ ID NO 29
<211> LENGTH: 11
<212> TYPE: PRT
<213> ORGANISM: Homo sapiens

<400> SEQUENCE: 29

Lys Ala Ser Gln Asp Val Asn Ile Ala Val Ala
1               5                   10

<210> SEQ ID NO 30
<211> LENGTH: 11
<212> TYPE: PRT
<213> ORGANISM: Homo sapiens

<400> SEQUENCE: 30

Arg Ala Ser Glu Asn Ile Tyr Tyr Ser Leu Ala
1               5                   10

<210> SEQ ID NO 31
<211> LENGTH: 11
<212> TYPE: PRT
<213> ORGANISM: Homo sapiens

<400> SEQUENCE: 31

Lys Ala Ser Gln Asp Val Asn Thr Ala Val Ala
1               5                   10

<210> SEQ ID NO 32
<211> LENGTH: 7
<212> TYPE: PRT
<213> ORGANISM: Homo sapiens

<400> SEQUENCE: 32

Ala Ala Ser Thr Leu Asp Ser
1               5

<210> SEQ ID NO 33
<211> LENGTH: 7
<212> TYPE: PRT
<213> ORGANISM: Homo sapiens

<400> SEQUENCE: 33

Trp Ala Ser Thr Arg His Thr
1               5

<210> SEQ ID NO 34

```
<211> LENGTH: 7
<212> TYPE: PRT
<213> ORGANISM: Homo sapiens

<400> SEQUENCE: 34

Asn Ala Asn Ser Leu Glu Asp
1               5

<210> SEQ ID NO 35
<211> LENGTH: 7
<212> TYPE: PRT
<213> ORGANISM: Homo sapiens

<400> SEQUENCE: 35

Ser Ala Ser Tyr Arg Tyr Thr
1               5

<210> SEQ ID NO 36
<211> LENGTH: 6
<212> TYPE: PRT
<213> ORGANISM: Homo sapiens

<400> SEQUENCE: 36

Tyr Ala Asn Tyr Pro Pro
1               5

<210> SEQ ID NO 37
<211> LENGTH: 6
<212> TYPE: PRT
<213> ORGANISM: Homo sapiens

<400> SEQUENCE: 37

His Tyr Asn Thr Pro Trp
1               5

<210> SEQ ID NO 38
<211> LENGTH: 6
<212> TYPE: PRT
<213> ORGANISM: Homo sapiens

<400> SEQUENCE: 38

Ala Tyr Asp Val Pro Tyr
1               5

<210> SEQ ID NO 39
<211> LENGTH: 6
<212> TYPE: PRT
<213> ORGANISM: Homo sapiens

<400> SEQUENCE: 39

His Tyr Ser Thr Pro Cys
1               5

<210> SEQ ID NO 40
<211> LENGTH: 1035
<212> TYPE: PRT
<213> ORGANISM: Homo sapiens

<400> SEQUENCE: 40

Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala Tyr Asn Leu
                20                  25                  30

Asp Pro Gln Arg Pro Val His Phe Gln Gly Pro Ala Asp Ser Phe Phe
            35                  40                  45
```

```
Gly Tyr Ala Val Leu Glu His Phe His Asp Asn Thr Arg Trp Val Leu
    50                  55                  60

Val Gly Ala Pro Lys Ala Asp Ser Lys Tyr Ser Pro Ser Val Lys Ser
65                  70                  75                  80

Pro Gly Ala Val Phe Lys Cys Arg Val His Thr Asn Pro Asp Arg Arg
                85                  90                  95

Cys Thr Glu Leu Asp Met Ala Arg Gly Lys Asn Arg Gly Thr Ser Cys
            100                 105                 110

Gly Lys Thr Cys Arg Glu Asp Arg Asp Glu Trp Met Gly Val Ser
        115                 120                 125

Leu Ala Arg Gln Pro Lys Ala Asp Gly Arg Val Leu Ala Cys Ala His
    130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175

Ile Pro Cys Tyr Glu Glu Tyr Lys Lys Lys Tyr Gly Glu Glu His Gly
            180                 185                 190

Ser Cys Gln Ala Gly Ile Ala Gly Phe Phe Thr Glu Glu Leu Val Val
        195                 200                 205

Met Gly Ala Pro Gly Ser Phe Tyr Trp Ala Gly Thr Ile Lys Val Leu
    210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
            260                 265                 270

Gly Ile Gly Lys Val Tyr Ile Phe Arg Ala Asp Arg Arg Ser Gly Thr
        275                 280                 285

Leu Ile Lys Ile Phe Gln Ala Ser Gly Lys Lys Met Gly Ser Tyr Phe
    290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335

Val Thr Val Tyr Ile Asn Arg Gly Asn Gly Ala Leu Glu Glu Gln Leu
            340                 345                 350

Ala Leu Thr Gly Asp Gly Ala Tyr Asn Ala His Phe Gly Glu Ser Ile
        355                 360                 365

Ala Ser Leu Asp Asp Leu Asp Asn Asp Gly Phe Pro Asp Val Ala Ile
    370                 375                 380

Gly Ala Pro Lys Glu Asp Asp Phe Ala Gly Ala Val Tyr Ile Tyr His
385                 390                 395                 400

Gly Asp Ala Gly Gly Ile Val Pro Gln Tyr Ser Met Lys Leu Ser Gly
                405                 410                 415

Gln Lys Ile Asn Pro Val Leu Arg Met Phe Gly Gln Ser Ile Ser Gly
            420                 425                 430

Gly Ile Asp Met Asp Gly Asn Gly Tyr Pro Asp Val Thr Val Gly Ala
        435                 440                 445

Phe Met Ser Asp Ser Val Val Leu Leu Arg Ala Arg Pro Val Ile Thr
    450                 455                 460

Val Asp Val Ser Ile Phe Leu Pro Gly Ser Ile Asn Ile Thr Ala Pro
```

```
                465                 470                 475                 480
            Gln Cys His Asp Gly Gln Gln Pro Val Asn Cys Leu Asn Val Thr Thr
                            485                 490                 495

Cys Phe Ser Phe His Gly Lys His Val Pro Gly Glu Ile Gly Leu Asn
                        500                 505                 510

Tyr Val Leu Met Ala Asp Val Ala Lys Lys Glu Lys Gly Gln Met Pro
                        515                 520                 525

Arg Val Tyr Phe Val Leu Leu Gly Glu Thr Met Gly Gln Val Thr Glu
                        530                 535                 540

Lys Leu Gln Leu Thr Tyr Met Glu Glu Thr Cys Arg His Tyr Val Ala
            545                 550                 555                 560

His Val Lys Arg Arg Val Gln Asp Val Ile Ser Pro Ile Val Phe Glu
                            565                 570                 575

Ala Ala Tyr Ser Leu Ser Glu His Val Thr Gly Glu Glu Arg Glu
                        580                 585                 590

Leu Pro Pro Leu Thr Pro Val Leu Arg Trp Lys Lys Gly Gln Lys Ile
                        595                 600                 605

Ala Gln Lys Asn Gln Thr Val Phe Glu Arg Asn Cys Arg Ser Glu Asp
                        610                 615                 620

Cys Ala Ala Asp Leu Gln Leu Gln Gly Lys Leu Leu Leu Ser Ser Met
            625                 630                 635                 640

Asp Glu Lys Thr Leu Tyr Leu Ala Leu Gly Ala Val Lys Asn Ile Ser
                        645                 650                 655

Leu Asn Ile Ser Ile Ser Asn Leu Gly Asp Asp Ala Tyr Asp Ala Asn
                        660                 665                 670

Val Ser Phe Asn Val Ser Arg Glu Leu Phe Phe Ile Asn Met Trp Gln
                        675                 680                 685

Lys Glu Glu Met Gly Ile Ser Cys Glu Leu Leu Glu Ser Asp Phe Leu
                        690                 695                 700

Lys Cys Ser Val Gly Phe Pro Phe Met Arg Ser Lys Ser Lys Tyr Glu
            705                 710                 715                 720

Phe Ser Val Ile Phe Asp Thr Ser His Leu Ser Gly Glu Glu Val
                            725                 730                 735

Leu Ser Phe Ile Val Thr Ala Gln Ser Gly Asn Thr Glu Arg Ser Glu
                        740                 745                 750

Ser Leu His Asp Asn Thr Leu Val Leu Met Val Pro Leu Met His Glu
                        755                 760                 765

Val Asp Thr Ser Ile Thr Gly Ile Met Ser Pro Thr Ser Phe Val Tyr
                        770                 775                 780

Gly Glu Ser Val Asp Ala Ala Asn Phe Ile Gln Leu Asp Asp Leu Glu
            785                 790                 795                 800

Cys His Phe Gln Pro Ile Asn Ile Thr Leu Gln Val Tyr Asn Thr Gly
                        805                 810                 815

Pro Ser Thr Leu Pro Gly Ser Ser Val Ser Ile Ser Phe Pro Asn Arg
                        820                 825                 830

Leu Ser Ser Gly Gly Ala Glu Met Phe His Val Gln Glu Met Val Val
                        835                 840                 845

Gly Gln Glu Lys Gly Asn Cys Ser Phe Gln Lys Asn Pro Thr Pro Cys
                        850                 855                 860

Ile Ile Pro Gln Glu Gln Asn Ile Phe His Thr Ile Phe Ala Phe
            865                 870                 875                 880

Phe Thr Lys Ser Gly Arg Lys Val Leu Asp Cys Glu Lys Pro Gly Ile
                            885                 890                 895
```

```
Ser Cys Leu Thr Ala His Cys Asn Phe Ser Ala Leu Ala Lys Glu Glu
            900                 905                 910

Ser Arg Thr Ile Asp Ile Tyr Met Leu Leu Asn Thr Glu Ile Leu Lys
        915                 920                 925

Lys Asp Ser Ser Val Ile Gln Phe Met Ser Arg Ala Lys Val Lys
    930                 935                 940

Val Asp Pro Ala Leu Arg Val Val Glu Ile Ala His Gly Asn Pro Glu
945                 950                 955                 960

Glu Val Thr Val Val Phe Glu Ala Leu His Asn Leu Glu Pro Arg Gly
            965                 970                 975

Tyr Val Val Gly Trp Ile Ile Ala Ile Ser Leu Leu Val Gly Ile Leu
        980                 985                 990

Ile Phe Leu Leu Leu Ala Val Leu  Leu Trp Lys Met Gly Phe Phe Arg
        995                 1000                1005

Arg Arg  Tyr Lys Glu Ile Ile  Glu Ala Glu Lys Asn  Arg Lys Glu
    1010                1015                1020

Asn Glu  Asp Ser Trp Asp Trp  Val Gln Lys Asn Gln
    1025                1030                1035

<210> SEQ ID NO 41
<211> LENGTH: 5
<212> TYPE: PRT
<213> ORGANISM: Homo sapiens

<400> SEQUENCE: 41

Gly Tyr Gly Val Asn
1               5

<210> SEQ ID NO 42
<211> LENGTH: 17
<212> TYPE: PRT
<213> ORGANISM: Homo sapiens

<400> SEQUENCE: 42

Met Ile Trp Gly Asp Gly Ile Thr Glu Tyr Asn Ser Ala Leu Lys Ser
1               5                   10                  15

Arg

<210> SEQ ID NO 43
<211> LENGTH: 10
<212> TYPE: PRT
<213> ORGANISM: Homo sapiens

<400> SEQUENCE: 43

Asp Ala Ser Ser Gly Tyr Gly Phe Ala Tyr
1               5                   10

<210> SEQ ID NO 44
<211> LENGTH: 12
<212> TYPE: PRT
<213> ORGANISM: Homo sapiens

<400> SEQUENCE: 44

Thr Ala Ser Ser Ser Val Ser Ser Ser Tyr Leu His
1               5                   10

<210> SEQ ID NO 45
<211> LENGTH: 7
<212> TYPE: PRT
<213> ORGANISM: Homo sapiens

<400> SEQUENCE: 45
```

Ser Thr Ser Asn Leu Ala Ser
1               5

<210> SEQ ID NO 46
<211> LENGTH: 6
<212> TYPE: PRT
<213> ORGANISM: Homo sapiens

<400> SEQUENCE: 46

Tyr His Arg Ser Pro Tyr
1               5

<210> SEQ ID NO 47
<211> LENGTH: 7
<212> TYPE: PRT
<213> ORGANISM: Homo sapiens

<400> SEQUENCE: 47

Ser Leu Ala Tyr Gly Leu Arg
1               5

<210> SEQ ID NO 48
<211> LENGTH: 7
<212> TYPE: PRT
<213> ORGANISM: Homo sapiens

<400> SEQUENCE: 48

Ser Val Val Tyr Gly Leu Arg
1               5

<210> SEQ ID NO 49
<211> LENGTH: 11
<212> TYPE: PRT
<213> ORGANISM: Homo sapiens

<400> SEQUENCE: 49

Cys Pro Glu Asp Gly Ile His Glu Leu Phe Pro
1               5                   10

<210> SEQ ID NO 50
<211> LENGTH: 116
<212> TYPE: PRT
<213> ORGANISM: Homo sapiens

<400> SEQUENCE: 50

Val Gln Leu Gln Glu Ser Gly Pro Glu Leu Val Lys Pro Gly Ala Ser
1               5                   10                  15

Val Lys Ile Pro Cys Lys Ala Ser Gly Tyr Thr Phe Thr Asp Tyr Asn
            20                  25                  30

Met Asp Trp Val Lys Gln Ser His Gly Lys Ser Leu Glu Trp Ile Gly
        35                  40                  45

Asp Ile Asn Pro Asn Asn Gly Gly Thr Ile Tyr Asn Gln Lys Phe Gln
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Thr Ala Val Tyr Tyr Cys Ala
                85                  90                  95

Arg Ser Gly Val Ile Ser Thr Asp Tyr Trp Gly Gln Gly Thr Thr Val
            100                 105                 110

Thr Val Ser Ser
        115

-continued

<210> SEQ ID NO 51
<211> LENGTH: 118
<212> TYPE: PRT
<213> ORGANISM: Homo sapiens

<400> SEQUENCE: 51

Val Gln Leu Gln Glu Ser Gly Gly Leu Val Lys Pro Gly Gly Ser
1               5                   10                  15

Leu Lys Leu Ser Cys Ala Ala Ser Gly Phe Thr Phe Ser Asp Tyr Tyr
                20                  25                  30

Met Tyr Trp Val Arg Gln Thr Pro Glu Lys Arg Leu Glu Trp Val Ala
            35                  40                  45

Thr Ile Ser Asp Gly Gly Asn Tyr Thr Tyr Tyr Pro Asp Ser Val Lys
    50                  55                  60

Gly Arg Phe Thr Ile Ser Arg Asp Asn Ala Lys Asn Asn Leu Tyr Leu
65                  70                  75                  80

Gln Met Ser Ser Leu Lys Ser Glu Asp Thr Ala Met Tyr Tyr Cys Ala
                85                  90                  95

Arg Asp Arg Asp Gly Ser Ser Leu Phe Ala Tyr Trp Gly Gln Gly Thr
            100                 105                 110

Thr Val Thr Val Ser Ser
        115

<210> SEQ ID NO 52
<211> LENGTH: 119
<212> TYPE: PRT
<213> ORGANISM: Homo sapiens

<400> SEQUENCE: 52

Val Lys Leu Gln Glu Ser Gly Ala Glu Leu Val Lys Pro Gly Ala Ser
1               5                   10                  15

Val Lys Leu Ser Cys Thr Ala Ser Gly Phe Asn Ile Lys Asp Thr Tyr
                20                  25                  30

Val His Trp Val Lys Gln Arg Pro Glu Gln Gly Leu Glu Trp Ile Gly
            35                  40                  45

Asn Ile Asp Pro Ala Asn Gly Asn Thr Lys Tyr Asp Pro Lys Phe Gln
    50                  55                  60

Gly Lys Ala Thr Ile Thr Ala Asp Thr Ser Asn Thr Ala Tyr Leu
65                  70                  75                  80

His Leu Ser Ser Leu Thr Ser Glu Asp Thr Ala Val Tyr Tyr Cys Ala
                85                  90                  95

Arg Trp Leu Arg His Phe Tyr Tyr Ala Met Asp Tyr Trp Gly Gln Gly
            100                 105                 110

Thr Thr Val Thr Val Ser Ser
        115

<210> SEQ ID NO 53
<211> LENGTH: 116
<212> TYPE: PRT
<213> ORGANISM: Homo sapiens

<400> SEQUENCE: 53

Val Lys Leu Gln Gln Ser Gly Pro Gly Leu Val Ala Pro Ser Gln Ser
1               5                   10                  15

Leu Ser Ile Thr Cys Thr Val Ser Gly Phe Ser Leu Thr Ser Tyr Gly
                20                  25                  30

Val His Trp Val Arg Gln Pro Pro Gly Lys Gly Leu Glu Trp Leu Gly
            35                  40                  45

```
Val Ile Trp Ser Gly Gly Ser Thr Asn Tyr Asn Ser Ala Leu Met Ser
     50                  55                  60

Arg Leu Ser Ile Ser Lys Asp Asn Phe Lys Ser Gln Val Phe Leu Lys
 65                  70                  75                  80

Met Asn Ser Leu Gln Thr Asp Asp Thr Ala Ile Tyr Tyr Cys Ala Arg
                 85                  90                  95

Asp Tyr Gly Asn Tyr Pro Trp Phe Ala Tyr Trp Gly Gln Gly Thr Thr
                100                 105                 110

Val Thr Val Ser
            115

<210> SEQ ID NO 54
<211> LENGTH: 117
<212> TYPE: PRT
<213> ORGANISM: Homo sapiens

<400> SEQUENCE: 54

Val Lys Leu Gln Glu Ser Gly Pro Gly Leu Val Ala Pro Ser Gln Ser
  1               5                  10                  15

Leu Ser Ile Thr Cys Thr Val Ser Gly Phe Ser Leu Thr Gly Tyr Gly
                 20                  25                  30

Val Asn Trp Val Arg Gln Pro Pro Gly Lys Gly Leu Glu Trp Leu Gly
             35                  40                  45

Met Ile Trp Gly Asp Gly Ile Thr Glu Tyr Asn Ser Ala Leu Lys Ser
     50                  55                  60

Arg Leu Ser Ile Ser Lys Asp Asn Ser Lys Ser Gln Val Phe Leu Lys
 65                  70                  75                  80

Met Asn Ser Leu Gln Thr Asp Asp Thr Ala Arg Tyr Tyr Cys Ala Arg
                 85                  90                  95

Asp Ala Ser Ser Gly Tyr Gly Phe Ala Tyr Trp Gly Gln Gly Thr Thr
                100                 105                 110

Val Thr Val Ser Ser
            115

<210> SEQ ID NO 55
<211> LENGTH: 108
<212> TYPE: PRT
<213> ORGANISM: Homo sapiens

<400> SEQUENCE: 55

Asp Ile Gln Met Thr Gln Ser Pro Pro Ser Leu Ser Ala Ser Leu Gly
  1               5                  10                  15

Glu Arg Val Ser Leu Thr Cys Arg Ala Ser Gln Glu Ile Ser Gly Tyr
                 20                  25                  30

Leu Ile Trp Leu Gln Gln Lys Pro Asp Gly Thr Ile Gln Arg Leu Ile
             35                  40                  45

Tyr Ala Ala Ser Thr Leu Asp Ser Gly Val Pro Lys Arg Phe Ser Gly
     50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Asn Tyr Pro Pro
                 85                  90                  95

Thr Phe Gly Gly Gly Thr Lys Leu Glu Ile Lys Arg
                100                 105

<210> SEQ ID NO 56
<211> LENGTH: 107
```

```
<212> TYPE: PRT
<213> ORGANISM: Homo sapiens

<400> SEQUENCE: 56

His Pro Asp Asp Thr Val Ser Lys Phe Met Ser Thr Ser Val Gly Asp
1               5                   10                  15

Arg Val Ser Ile Thr Cys Lys Ala Ser Gln Asp Val Asn Ile Ala Val
            20                  25                  30

Ala Trp Tyr Gln Gln Arg Pro Gly Gln Ser Pro Lys Leu Leu Ile Tyr
        35                  40                  45

Trp Ala Ser Thr Arg His Thr Gly Val Pro Asp Arg Phe Thr Gly Ser
    50                  55                  60

Gly Ser Gly Thr Asp Tyr Thr Leu Thr Ile Ser Ser Val Gln Ala Glu
65                  70                  75                  80

Asp Leu Ala Leu Tyr Tyr Cys Gln Gln His Tyr Asn Thr Pro Trp Thr
                85                  90                  95

Phe Gly Gly Gly Thr Lys Leu Glu Ile Lys Arg
            100                 105

<210> SEQ ID NO 57
<211> LENGTH: 108
<212> TYPE: PRT
<213> ORGANISM: Homo sapiens

<400> SEQUENCE: 57

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Ala Asn Ser Leu Glu Asp Gly Val Pro Ser Arg Phe Ser Gly
    50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Lys Gln Ala Tyr Asp Val Pro Tyr
                85                  90                  95

Thr Phe Gly Gly Gly Thr Lys Leu Glu Leu Lys Arg
            100                 105

<210> SEQ ID NO 58
<211> LENGTH: 107
<212> TYPE: PRT
<213> ORGANISM: Homo sapiens

<400> SEQUENCE: 58

His Pro Asp Asp Thr Val Ser Lys Phe Met Ser Thr Ser Val Gly Asp
1               5                   10                  15

Arg Val Ser Ile Thr Cys Lys Ala Ser Gln Asp Val Asn Thr Ala Val
            20                  25                  30

Ala Trp Tyr Gln Gln Lys Pro Gly Gln Ser Pro Lys Leu Leu Ile Tyr
        35                  40                  45

Ser Ala Ser Tyr Arg Tyr Thr Gly Val Pro Asp Arg Phe Thr Gly Ser
    50                  55                  60

Gly Ser Gly Thr Asp Phe Thr Phe Thr Ile Ser Ser Val Gln Ala Glu
65                  70                  75                  80

Asp Leu Ala Val Tyr Tyr Cys Gln Gln His Tyr Ser Thr Pro Cys Ala
                85                  90                  95
```

```
Phe Gly Gly Gly Thr Lys Leu Glu Ile Lys Arg
            100                 105

<210> SEQ ID NO 59
<211> LENGTH: 109
<212> TYPE: PRT
<213> ORGANISM: Homo sapiens

<400> SEQUENCE: 59

Tyr Ile Val Leu Thr Gln Ser Pro Ala Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Leu Glu Ile Lys Arg
            100                 105
```

ANTIHUMAN α9 INTEGRIN ANTIBODY AND USE OF THE SAME

TECHNICAL FIELD

The present invention relates to: an antibody (particularly a monoclonal antibody), a chimeric antibody, a humanized antibody and a human antibody, which specifically recognize human α9 integrin; a hybridoma cell which produces the monoclonal antibody; a method for producing the monoclonal antibody; a method for producing the hybridoma cell; a therapeutic agent comprising the anti-human α9 integrin antibody; a diagnostic agent comprising the human α9 integrin antibody; a method for screening a compound which inhibits the activity of human α9 integrin; and the like.

BACKGROUND ART

A cell is the minimum functional unit for exhibit life phenomenon. In an organism, cells having the same function assemble to constitute tissue, various types of tissues get together and cooperate to form an organ having a certain function, and the whole performs harmonious and unified vital activity. Many types of tissues are basically constituted by cells and extracellular matrices, and such a constitution is held by cells, cells adhering with extracellular matrix, extracellular matrix-extracellular matrix adhesion and cell-cell adhesion. It was thought that extracellular matrices have no bioactivity and are just fillers, but it has been becoming clear that they actually play an important role in almost all types of tissues. After cell-extracellular matrix adhesion activity was known, it was suggested that extracellular matrices not only play a role as a foothold for cells, but also are involved in the regulation of various cellular functions and the maintenance of homeostasis of tissues and organs. The importance of extracellular matrices has been more widely understood.

Cell-extracellular matrix adhesion is provided via a transmembrane cell-adhesion protein (typically integrin). Integrin is constituted by a heterodimer (α chain:β chain=1:1). 18 types of α chains and 8 types of β chains have been found, and at least 24 combinations thereof have been identified. It is known that each integrin recognizes a specific extracellular matrix (ligand). Moreover, it has been clarified that transmembrane cell-adhesion protein including integrin not only plays a role in cell-extracellular matrix adhesion/fixation, but also plays a role in converting information from extracellular matrices into intracellular signal to regulate proliferation, motility, death, differentiation, etc. of cells.

Integrins are classified into subfamilies based on specificity and function to ligand as follows: a collagen receptor; a laminin receptor; an RGD receptor recognizing an Arg-Gly-Asp (RGD) sequence contained in fibronectin, bitronectin or the like; and a leucocyte-specific receptor which is present only in leucocyte (Hynes R O. 2002. Integrins: Bidirectional, Allosteric Signaling Machines. Cell 110: 673-87; Miyasaka M. 2000. New edition of Adhesion Molecule handbook. Shujunsya). α4 and α9 integrins do not belong to the above-described subfamilies, and the subfamily thereof is referred to as α4 integrin subfamily (Elise L. Palmer, Curzio Rfiegg, Ronald Ferrando, Robert Pytela, Sheppard D. 1993. Sequence and Tissue Distribution of the Integrin α9 Subunit, a Novel Partner of 131 That Is Widely Distributed in Epithelia and Muscle. The Journal of Cell Biology 123: 1289-97).

Osteopontin (hereinafter abbreviated as OPN), which is one of extracellular matrices (ECM), is a secreted and acidic phosphorylated glycoprotein having the molecular weight of about 41 kDa. Expression of the molecule is widely recognized in breast fluid, urine, renal tubule, osteoclasts, osteoblasts, macrophages, activated T cells, tumor tissues, etc. The center portion of the molecule has: a cell-adhesive sequence GRGDS; and a SVVYGLR (SEQ ID NO:48) sequence (in human OPN) or a SLAYGLR (SEQ ID NO:47) sequence (in mouse OPN). Immediately after the position, there is a thrombin cleavage site. The molecule adheres to an integrin as an RGD receptor via the GRGDS sequence, and adheres to α4 (α4β1) and α9 (α9β1) integrins via the SVVYGLR (SEQ ID NO:48) sequence or the SLAYGLR sequence.

α4β1 binds to both a non-thrombin-cleaved OPN (non-cleaved OPN) and a thrombin-cleaved N-terminal fragment (cleaved OPN), while α9β1 only binds to a cleaved OPN. This difference of manner has already been found (Y Yokosaki et al., (1999) The Journal of Biological Chemistry 274, 36328-36334; P. M. Green et al., (2001) FEBS Letters 503, 75-79; S. T. Barry et al., (2000) Experimental Cell Research 258, 342-351). α4 and α9 integrins have many common ligands other than OPN. For example, an EDA site of fibronectin, a propeptide-von Willebrand factor (pp-vWF), tissue-type transglutaminase (tTG), blood coagulation factor XIII and Vascular Cell Adhesion Molecule-1 (VCAM-1) are known. Further, as a ligand specifically recognized by α4 integrin, CS-1 domain of fibronectin, MadCAM-1(α4β7) and the like are known. As a ligand specifically recognized by α9 integrin, tenascin C, plasmin and the like are known.

Amino acid sequences of α4 and α9 integrins and β1 integrin subunit are publicly known and are registered in GenBank. Further, it is known that amino acid sequences of these integrins have high similarity among species.

International Publication WO02/081522 discloses therapeutic effects on rheumatism-like arthritis and hepatitis by suppression of OPN function using an OPN-deficient mouse and a neutralization antibody to OPN. This publication also discloses that the SVVYGLR sequence, which is a recognition sequence of α4 integrin and α9 integrin, is important for onset of inflammatory diseases, and that a receptor to OPN is expressed in an immunocompetent cell and the like and is associated with inflammatory diseases.

DISCLOSURE OF THE INVENTION

At present, various therapeutic agents for cancer, inflammatory disease, infection disease, autoimmune disease and bone disease are known. However, the development of prophylactic agents and/or therapeutic agents for cancer, inflammatory disease, infection disease, autoimmune disease and bone disease having improved therapeutic effects has been desired.

The present inventors focused their attention on integrin, in particular α9 integrin, and made various studies to find that a specific inhibitory antibody to α9 integrin has cancer suppression effects and anti-inflammatory effects, and thus the present invention was achieved. In particular, the present invention provides an anti-human α9 integrin antibody, a cell producing the same, a therapeutic agent comprising the antibody, a method for screening a compound which inhibits the activity of α9 integrin and the like as described below:

(1) An anti-human α9 integrin antibody which recognizes one or more amino acid sequences selected from the group consisting of the amino acid sequences set forth in SEQ ID NOs: 1, 2, 3, 4, 5, 6, 7, 8, 9, 10, 11, 12, 13, 14 and 15.

(2) An anti-human α9 integrin antibody, wherein in the heavy-chain complementarity determining region (CDRH): CDRH1 is the amino acid sequence set forth in SEQ ID NO: 16, 17, 18, 19 or 41; CDRH2 is the amino acid sequence set forth in SEQ ID NO: 20, 21, 22, 23 or 42; and CDRH3 is the amino acid sequence set forth in SEQ ID NO: 24, 25, 26, 27 or 43, and wherein in the light-chain complementarity determining region (CDRL): CDRL1 is the amino acid sequence set forth in SEQ ID NO: 28, 29, 30, 31 or 44; CDRL2 is the amino acid sequence set forth in SEQ ID NO: 32, 33, 34, 35 or 45; and CDRL3 is the amino acid sequence set forth in SEQ ID NO: 36, 37, 38, 39 or 46.

(3) An anti-human α9 integrin antibody having at least one of the complementarity determining regions (CDRs) comprising the amino acid sequence set forth in SEQ ID NO: 16, 20, 24, 28, 32 or 36.

(4) An anti-human α9 integrin antibody having all of the complementarity determining regions (CDRs) comprising the amino acid sequence set forth in SEQ ID NO: 16, 20, 24, 28, 32 or 36.

(5) An anti-human α9 integrin antibody having at least one of the complementarity determining regions (CDRs) comprising the amino acid sequence set forth in SEQ ID NO: 17, 21, 25, 29, 33 or 37.

(6) An anti-human α9 integrin antibody having all of the complementarity determining regions (CDRs) comprising the amino acid sequence set forth in SEQ ID NO: 17, 21, 25, 29, 33 or 37.

(7) An anti-human α9 integrin antibody having at least one of the complementarity determining regions (CDRs) comprising the amino acid sequence set forth in SEQ ID NO: 18, 22, 26, 30, 34 or 38.

(8) An anti-human α9 integrin antibody having all complementarity determining regions (CDRs) comprising the amino acid sequence set forth in SEQ ID NO: 18, 22, 26, 30, 34 or 38.

(9) An anti-human α9 integrin antibody having at least one of the complementarity determining regions (CDRs) comprising the amino acid sequence set forth in SEQ ID NO: 19, 23, 27, 31, 35 or 39.

(10) An anti-human α9 integrin antibody having all of the complementarity determining regions (CDRs) comprising the amino acid sequence set forth in SEQ ID NO: 19, 23, 27, 31, 35 or 39.

(11) An anti-human α9 integrin antibody having at least one of the complementarity determining region (CDR) comprising the amino acid sequence set forth in SEQ ID NO: 41, 42, 43, 44, 45 or 46.

(12) An anti-human α9 integrin antibody having all of the complementarity determining regions (CDRs) comprising the amino acid sequence set forth in SEQ ID NO: 41, 42, 43, 44, 45 or 46.

(13) The anti-human α9 integrin antibody according to any one of items (1) to (12), which inhibits binding between human α9 integrin and ligand of α9 integrin.

(14) The anti-human α9 integrin antibody according to any one of items (1) to (13), which is produced by a hybridoma cell having accession No. FERM BP-10510, FERM BP-10511, FERM BP-10512, FERM BP-10513 or FERM BP-10832.

(15) The anti-human α9 integrin antibody according to any one of items (1) to (14), which is a monoclonal antibody.

(16) The anti-human α9 integrin antibody according to any one of items (1) to (13), which is a chimeric antibody.

(17) The anti-human α9 integrin antibody according to any one of items (1) to (13), which is a humanized antibody.

(18) The anti-human α9 integrin antibody according to any one of items (1) to (13), which is a human antibody.

(19) A therapeutic agent for cancer, inflammatory disease, infection disease, autoimmune disease or bone disease, which comprises the anti-human α9 integrin antibody according to any one of items (1) to (18) as an active ingredient.

(20) A therapeutic agent for cancer, inflammatory disease, infection disease, autoimmune disease or bone disease, which comprises both the anti-human α9 integrin antibody according to any one of items (1) to (18) and an anti-human α4 integrin antibody as active ingredients.

(21) A diagnostic agent for cancer, inflammatory disease, infection disease, autoimmune disease or bone disease, which comprises the anti-human α9 integrin antibody according to any one of items (1) to (18) as an active ingredient.

(22) A method for screening a compound which inhibits the activity of α9 integrin, wherein a peptide comprising one or more amino acid sequences selected from the group consisting of the amino acid sequences set forth in SEQ ID NOs: 1, 2, 3, 4, 5, 6, 7, 8, 9, 10, 11, 12, 13, 14 and 15 is used.

Effect of the Invention

The antibody of the present invention suppresses the α9 integrin function and thereby elicits therapeutic effects on cancer (e.g., proliferation and metastasis of cancer cells), inflammatory disease (e.g., rheumatoid arthritis, osteoarthritis, hepatitis, bronchial asthma, fibrosis, diabetes, arteriosclerosis, multiple sclerosis, and inflammatory bowel disease (ulcerative colitis, Crohn's disease)), infection disease (e.g., hepatitis), autoimmune disease (e.g., systemic lupus erythematosus, polymyositis, autoimmune thyroid disease, tubulointerstitial nephritis, and myasthenia gravis), bone disease (e.g., osteoporosis) and the like. Additionally, a pharmaceutical composition comprising both the anti-α9 integrin antibody of the present invention and an anti-α4 integrin antibody results in further improved therapeutic effects on cancer, inflammatory disease and the like. The antibody of the present invention can also be utilized as a diagnostic agent since expression of α9 integrin in a cell or tissue can be pathologically detected using the antibody.

BRIEF DESCRIPTION OF THE DRAWINGS

FIG. 1 (FIG. 1-1 and FIG. 1-2) shows results of analysis of complementarity determining region (CDR) of anti-human α9 integrin antibody.

FIG. 5 shows results of examination of therapeutic effects on arthritis with anti-mouse α9 integrin antibody using a mouse model of arthritis.

FIG. 7 shows results of examination of therapeutic effects with anti-α9 integrin antibody after the onset of arthritis.

FIG. 9 shows results of measurement of expression of IL-17 and RORγt in the inguinal lymph node of mouse, which was conducted in order to examine involvement of Th17 in a mouse model of arthritis.

BEST MODE FOR CARRYING OUT THE INVENTION

[Process of the Invention]

Figure 2:
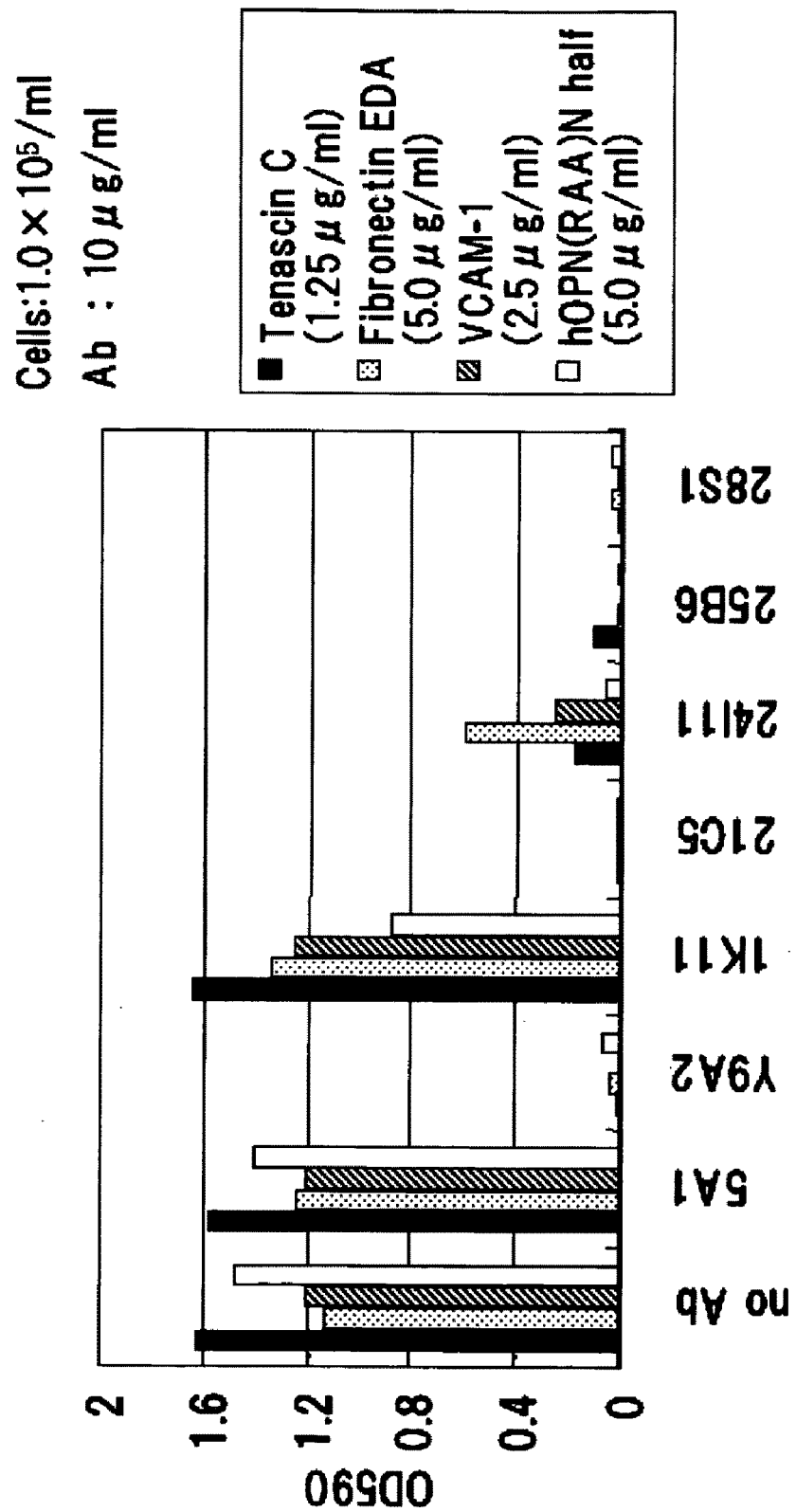
FIG. 2 shows results of examination of cell adhesion inhibition effects with 5 clones of anti-human α9 integrin antibody using human α9 integrin expressing cells.

Regarding Tysabri (registered trademark, natalizumab), which is an antibody to α4 integrin, application for approval thereof as a therapeutic agent for multiple sclerosis was filed by Biogen Idec Inc. (Massachusetts, US) and Elan Corporation (Ireland), and it was approved by Food and Drug Administration (FDA) in November 2004. Further, Tysabri (registered trademark) has been clinically developed, targeting diseases such as Crohn's disease and rheumatism-like arthritis. An anti-human α4 μl integrin monoclonal antibody called P4C2 is used in the laboratory.

As an antibody to α9 integrin, a monoclonal antibody called Y9A2, which shows specificity to α9 integrins of human and guinea pig (A. Wang et al., (1996) Am. J. Respir., Cell Mol. Biol. 15. 664-672), is provided for experiments, but it is not clinically used.

According to the present invention, an antibody which specifically reacts with human α9 integrin was successfully obtained by carefully carrying out the procedures described below.

(1) Preparation of Cell Line which Provides Human α9 Integrin Overexpression

In order to prepare an antibody to α9 integrin, gene introduction was applied to a CHO-K1 cell, which is a cell from the ovary of hamster, and a cell line overexpressing human α9 integrin was established. A mouse was immunized with the cell as an antigen.

(2) Screening of Hybridoma

In order to efficiently obtain a clone which only reacts with human α9 integrin from various hybridomas obtained by cell fusion, a CHO-K1 cell, in which human α4 integrin that belongs to the same integrin family was expressed, was used to select a clone, which does not show crossreactivity with other integrins, and which does not react with a cell surface antigen of the parent cell (CHO-K1). Thus, an inhibitory antibody which specifically reacts with human α9 integrin was efficiently obtained.

[Anti-α9 Integrin Antibody of the Present Invention]

The present invention provides a monoclonal antibody to human α9 integrin. As used herein, the term "antibody" means an entire antibody molecule, which may bind to α9 integrin as an antigen or a partial peptide thereof, or a fragment thereof (e.g., fragments such as Fab, Fab' and F(ab')$_2$), and it may be a polyclonal or monoclonal antibody. Preferably, the "antibody" in the present invention means a monoclonal antibody. Further, in the present invention, the "antibody" includes a chimeric antibody, a humanized antibody and a human antibody.

The "monoclonal antibody" in the present invention is highly specific to an antigen and recognizes a single antigen.

As used herein, the term "antibody fragment" refers to a portion of a full-length antibody, and it means an antigen binding region or a variable region. For example, the "antibody fragment" includes Fab, Fab', F(ab')$_2$ and a Fv fragment. These antibody fragments can be prepared using a generally-known method such as papain digestion and pepsin digestion of antibody.

The term "chimeric antibody" refers to a human/mouse chimeric antibody in which the constant region of the anti-human α9 integrin antibody obtained in the present invention is modified by genetic engineering to be identical to the constant region of a human antibody (see EP Laid-Open Publication No. EP0125023). The term "humanized antibody" refers to an antibody in which the primary structure of the anti-human α9 integrin antibody obtained in the present invention except for the complementarity recognizing regions of H-chain and L-chain is modified by genetic engineering to correspond to the primary structure of human antibody. The term "human antibody" means a monoclonal antibody prepared using a transgenic animal into which a human gene involved in the production of antibody is introduced (see EP Laid-Open Publication No. EP0546073).

More specifically, the present invention provides an anti-human α9 integrin antibody which recognizes one or more amino acid sequences selected from the group consisting of the amino acid sequences set forth in SEQ ID NOs: 1, 2, 3, 4, 5, 6, 7, 8, 9, 10, 11, 12, 13, 14 and 15. According to a preferred embodiment, the antibody of the present invention recognizes at least 2, 3, 4 or 5 amino acid sequences or 6 amino acid sequences selected from the group consisting of the amino acid sequences set forth in SEQ ID NOs: 1, 2, 3, 4, 5, 6, 7, 8, 9, 10, 11, 12, 13, 14 and 15. Preferably, the antibody of the present invention specifically recognizes: (1) the amino acid sequences set forth in SEQ ID NOs: 2, 5, 7, 8, 10 and 11; (2) SEQ ID NO: 5; (3) SEQ ID NO: 7; (4) the amino acid sequences set forth in SEQ ID NOs: 1, 5, 6, 7 and 13; (5) the amino acid sequences set forth in SEQ ID NOs: 5, 7, 10 and 13; (6) the amino acid sequences set forth in SEQ ID NOs: 2, 5, 7, 8 and 15; (7) SEQ ID NOs: 5, 7, 10 and 13; or (8) the amino acid sequence set forth in SEQ ID NO: 11.

According to a preferred embodiment, the antibody of the present invention has at least one of the complementarity determining regions (CDRs) comprising the amino acid sequence set forth in SEQ ID NO: 16, 20, 24, 28, 32 or 36. More preferably, the antibody is an anti-human α9 integrin antibody having at least 2, 3, 4 or 5, or 6 of the complementarity determining regions (CDRs) comprising the amino acid sequence set forth in SEQ ID NO: 16, 20, 24, 28, 32 or 36. Particularly preferably, the antibody comprises: (1) the amino acid sequences set forth in SEQ ID NOs: 16, 20, 24 and 36; (2) the amino acid sequences set forth in SEQ ID NOs: 16, 20 and 24; (3) the amino acid sequences set forth in SEQ ID NOs: 28, 32 and 36; (4) the amino acid sequences set forth in SEQ ID NOs: 20 and 24; or (5) the amino acid sequences set forth in SEQ ID NOs: 24 and 36.

According to another embodiment, the antibody of the present invention has at least one of the complementarity determining regions (CDRs) comprising the amino acid sequence set forth in SEQ ID NO: 17, 21, 25, 29, 33 or 37. More preferably, the antibody is an anti-human α9 integrin antibody having at least 2, 3, 4 or 5, or 6 of the complementarity determining regions (CDRs) comprising the amino acid sequence set forth in SEQ ID NO: 17, 21, 25, 29, 33 or 37. Most preferably, the antibody comprises: (1) the amino acid sequences set forth in SEQ ID NOs: 17, 21, 25 and 37; (2) the amino acid sequences set forth in SEQ ID NOs: 17, 21 and 25; (3) the amino acid sequences set forth in SEQ ID NOs: 29, 33 and 37; (4) the amino acid sequences set forth in SEQ ID NOs: 21 and 25; or (5) the amino acid sequences set forth in SEQ ID NOs: 25 and 37.

According to another embodiment, the antibody of the present invention has at least one of the complementarity determining regions (CDRs) comprising the amino acid sequence set forth in SEQ ID NO: 18, 22, 26, 30, 34 or 38. More preferably, the antibody is an anti-human α9 integrin antibody having at least 2, 3, 4 or 5, or 6 of the complementarity determining regions (CDRs) comprising the amino acid sequence set forth in SEQ ID NO: 18, 22, 26, 30, 34 or 38. Particularly preferably, the antibody comprises: (1) the amino acid sequences set forth in SEQ ID NOs: 18, 22, 26 and 38; (2) the amino acid sequences set forth in SEQ ID NOs: 18, 22 and 26; (3) the amino acid sequences set forth in SEQ ID NOs: 30, 34 and 38; (4) the amino acid sequences set forth in SEQ ID NOs: 22 and 26; or (5) the amino acid sequences set forth in SEQ ID NOs: 26 and 38.

According to another embodiment, the antibody of the present invention has at least one of the complementarity determining regions (CDRs) comprising the amino acid sequence set forth in SEQ ID NO: 19, 23, 27, 31, 35 or 39. More preferably, the antibody is an anti-human α9 integrin antibody having at least 2, 3, 4 or 5, or 6 of the complementarity determining regions (CDRs) comprising the amino acid sequence set forth in SEQ ID NO: 19, 23, 27, 31, 35 or 39. Particularly preferably, the antibody comprises: (1) the amino acid sequences set forth in SEQ ID NOs: 19, 23, 27 and 39; (2) the amino acid sequences set forth in SEQ ID NOs: 19, 23 and 27; (3) the amino acid sequences set forth in SEQ ID NOs: 31, 35 and 39; (4) the amino acid sequences set forth in SEQ ID NOs: 23 and 27; or (5) the amino acid sequences set forth in SEQ ID NOs: 27 and 39.

According to another embodiment, the antibody of the present invention has at least one of the complementarity determining regions (CDRs) comprising the amino acid sequence set forth in SEQ ID NO: 41, 42, 43, 44, 45 or 46. More preferably, the antibody is an anti-human α9 integrin antibody having at least 2, 3, 4 or 5, or 6 of the complementarity determining regions (CDRs) comprising the amino acid sequence set forth in SEQ ID NO: 41, 42, 43, 44, 45 or 46. Particularly preferably, the antibody comprises: (1) the amino acid sequences set forth in SEQ ID NOs: 41, 42, 43 and 46; (2) the amino acid sequences set forth in SEQ ID NOs: 41, 42 and 43; (3) the amino acid sequences set forth in SEQ ID NOs: 44, 45 and 46; (4) the amino acid sequences set forth in SEQ ID NOs: 42 and 43; or (5) the amino acid sequences set forth in SEQ ID NOs: 43 and 46.

Particularly preferably, the antibody of the present invention is an anti-human α9 integrin antibody produced by a hybridoma cell having accession No. FERM BP-10510, FERM BP-10511, FERM BP-10512, FERM BP-10513 or FERM BP-10832.

Hereinafter, preparation of an anti-α9 integrin monoclonal antibody will be described in detail, but preparation of the antibody is not limited thereto.

[α9 Integrin (Antigen)]

In the present invention, α9 integrin to be used as an antigen may be: (1) a protein from any cell, which expresses α9 integrin from human or another mammal, or a protein from any tissue in which the cell is present; (2) a recombinant protein obtained by introducing gene DNA encoding α9 integrin (preferably cDNA) into a cell line of bacterium, yeast, animal or the like to cause expression; or (3) a synthetic protein.

Further, α9 integrin of the present invention comprises a polypeptide having an amino acid sequence which is substantially identical to amino acid sequences of α9 integrins of various mammals, in particular, the amino acid sequence of human α9 integrin (SEQ ID NO: 40).

As used herein, the phrase "polypeptide having an amino acid sequence which is substantially identical" means: a mutant polypeptide having an amino acid sequence in which several amino acids, preferably 1 to 10 amino acids, and particularly preferably 1 to several (e.g., 1 to 5, 1 to 4, 1 to 3, 1 to 2) amino acids are substituted, deleted, and/or modified in the amino acid sequence; and a mutant polypeptide having an amino acid sequence in which several amino acids, preferably 1 to 10 amino acids, and particularly preferably 1 to several (e.g., 1 to 5, 1 to 4, 1 to 3, 1 to 2) amino acids are added to the amino acid sequence of naturally occurring α9 integrin, and particularly preferably of α9 integrin from human, as long as it has biological characteristics which are substantially equivalent to those of naturally occurring α9 integrin, and particularly preferably those of α9 integrin from human. Moreover, it may be a mutant polypeptide having a plurality of such substitutions, deletions, modifications and additions.

α9 integrin of the present invention, in particular, α9 integrin from human can be produced by suitably using a method known in the art such as a chemical synthesis method and a cell culture method or a modified method thereof other than the genetic recombination technology.

Examples of methods for producing a mutant polypeptide include: a method for synthetic oligonucleotide site directed mutagenesis (gapped duplex method); a method for introducing point mutation randomly by nitrous acid or sulfurous acid treatment; a method for preparing a deletion mutant with Ba131 enzyme or the like; cassette mutagenesis; a linker scanning method; a misincorporation method; a mismatch primer method; and a DNA segment synthesis method.

Further, the α9 integrin of the present invention includes a "portion" of the α9 integrin. As used herein, the term "portion" refers to a portion comprising a region required for binding to α9 integrin ligand (e.g., OPN, tenascin-C, VCAM-1), and more specifically, a portion comprising positions 29 to 980 of the amino acid sequence set forth in SEQ ID NO: 1. The "portion" of the α9 integrin can be produced by the genetic recombination technology or chemical synthesis method according to the below-described method known in the art or a modified method thereof, or can also be produced by suitably cleaving α9 integrin, and particularly preferably α9 integrin from human isolated by cell culturing method using a proteolytic enzyme or the like.

As an antigen, a cell per se, which overexpresses α9 integrin on the cell membrane by the recombination technology, a membrane fraction thereof or the like can be used.

The α9 integrin of the present invention also includes a polypeptide having an amino acid sequence which is substantially identical to the amino acid sequence of human α9 integrin (SEQ ID NO: 40). Specifically, examples of polypeptides having an amino acid sequence which is substantially identical to the amino acid sequence set forth in SEQ ID NO: 40 include human α9 integrins having the amino acid sequence set forth in any of SEQ ID NOs: 1 to 15. In particular, in the present invention, a cell per se, which overexpresses human α9 integrin on the cell membrane by the recombination technology, is preferably used. Therefore, as described later, there is a case in which a gene encoding human α9 integrin (e.g., cDNA) is cloned using a known genetic engineering technique, and a cell per se, which overexpresses human α9 integrin on the cell membrane, or a cell membrane fraction thereof is prepared as an antigen.

[Preparation of Antibody Producing Cell]

An antigen is administered solely or in combination with a carrier and a diluent to a site of an animal to be immunized which can produce an antibody by the administration. In order to increase antibody-producing ability, a complete Freund's adjuvant or an incomplete Freund's adjuvant can be administered. The administration is generally carried out about 2 to 10 times (every 1 to 6 weeks). Examples of warm-blooded animals to be used include mouse, monkey, rabbit, dog, guinea pig, rat, hamster, sheep, goat, chicken, etc. In the present invention, mouse is preferably used.

When a subject to be treated is human and an animal which produces an α9 integrin inhibitory antibody is mouse, a human-mouse chimeric antibody or a humanized antibody is desirably used. More desirably, a human monoclonal antibody is prepared for use utilizing a transgenic animal such as mouse into which a human gene involved in antibody production is introduced.

[Cell Fusion Between Antibody Producing Cell and Myeloma Cell]

As a myeloma cell, a cell from mouse, rat, human or the like is used. Examples thereof include mouse myelomas P3U1, P3X63-Ag8, P3X63-Ag8-U1, P3NS1-Ag4, SP2/0-Ag14, P3X63-Ag8-653, etc. It is preferred that an antibody producing cell and a myeloma cell are derived from animals of the same species, in particular, of the same strain. A myeloma cell can be frozen for preservation or maintained by subculture in a general medium to which horse, rabbit or bovine fetal serum is added. It is preferred that a cell in the logarithmic growth phase is used for cell fusion. In the present invention, P3X63-Ag8-653 is preferably used.

Examples of methods for forming a hybridoma by fusing an antibody producing cell and a myeloma cell include a method using polyethylene glycol (PEG), a method using Sendai virus, and a method using an electrofusion apparatus. For example, in the case of the PEG method, splenic cells and myeloma cells may be suspended in a suitable medium or buffer solution containing about 30 to 60% PEG (average molecular weight: 1000 to 6000) in the mixing ratio of 1 to 10:1, preferably 5 to 10:1 to cause a reaction at about 25 to 37° C. at pH 6 to 8 for about 30 seconds to 3 minutes. After the reaction is completed, PEG solution is removed, and then the cells are resuspended in the medium and seeded in a cell well plate to continue culturing.

[Selection of Hybridoma Cell]

Selection of a hybridoma cell which produces a monoclonal antibody can be carried out according to a known method or a method corresponding thereto. Generally, it can be carried out in a medium for animal cells to which HAT (hypoxanthine, aminopterin, thymidine) is added. As a medium for selection and cultivation, any medium can be used as long as hybridoma cells can be grown therein. Examples of such media include: RPMI 1640 medium containing 1 to 20%, preferably 10 to 20% bovine fetal serum; GIT medium containing 1 to 10% bovine fetal serum (Wako Pure Chemical Industries, Ltd.); and serum-free medium for hybridoma culture (SFM-101, Nissui Pharmaceutical Co., Ltd.). Culture temperature is generally 20 to 40° C., and preferably about 37° C. Culture time is generally 5 days to 3 weeks, and preferably 1 to 2 weeks. Culture can be generally performed under 5% $CO_2$.

Production of the monoclonal antibody of the present invention can be confirmed and subjected to screening using the cell-ELISA method described in "Shin-rinsho Meneki Jikken Sousa-hou (New Clinical Immunization Experiment Operation Method)", Part 3, Kagaku Hyoronsha, 1997. In the case in which it is expected that the background becomes high and false-positive results are increased when using a cell used in immunization for screening, a clone, which reacts to human α9 integrin which is overexpressed in a cell different from that used in immunization, and which does not react to a cell which overexpresses human α4 integrin, can be used as an anti-human α9 integrin antibody. Such a clone may be repeatedly subjected to the limiting dilution once to 5 times, and preferably 2 to 4 times to prepare a monoclonal antibody.

[Separation/Purification of Antibody]

Antibodies obtained can be homogeneously purified. In order to separate/purify antibodies, a separation/purification method generally used for proteins may be used. For example, by suitably selecting and combining methods including, without limitation, a chromatography column of affinity chromatography or the like, a filter, ultrafiltration, salting-out, dialysis, SDS polyacrylamide gel electrophoresis, isoelectric focusing electrophoresis, etc., an antibody can be separated and purified (Antibodies: A Laboratory Manual. Ed Harlow and David Lane, Cold Spring Harbor Laboratory, 1988). Examples of columns for use in affinity chromatography include protein A column and protein G column. Examples of columns using the protein A column include Hyper D, POROS, Sepharose F. F. (Amersham Biosciences), etc.

[Labeling of Antibody]

The antibody obtained can be labeled in various manners using a known method or a commercially-available kit (e.g., biotin labeling, FITC labeling, and APC labeling). In the present invention, biotin labeling using Biotin Labeling Kit (Dojindo Laboratories) is preferably used.

The monoclonal antibody obtained in this way is, if necessary, purified, and after that, it may be formulated according to the ordinary method to be used as a prophylactic and/or therapeutic agent for cancer, inflammatory disease, infection disease, autoimmune disease, bone disease or the like. As a formulation of the prophylactic and/or therapeutic agent therefor, parenteral formulation such as an injectable solution and an agent for intravenous drip can be employed, and based on original ideas, the monoclonal antibody can be used in the form of oral formulation. In formulating, a carrier, a diluent, an additive or the like, which is suitable for a formulation, can be used within the range which is pharmacologically and pharmaceutically acceptable.

[Pharmacological Effects of Antibody]

It has been clarified that the role of integrin is not only adhesion/fixation between a cell and an extracellular matrix (ECM), but also conversion of information from extracellular matrix into intracellular signal and regulation of proliferation, motility, death, differentiation, etc. of cells. Since the obtained monoclonal antibody can block intracellular signal transduction of information from ECM by inhibiting binding between ECM and α9 integrin, diseases in which ECM is involved can be treated thereby. ECMs, which bind to α9 integrin, and α9 ligands, such as OPN, fibronectin, a propeptide-von Willebrand factor (pp-vWF), tissue-type transglutaminase (tTG), blood coagulation factor XIII, Vascular Cell Adhesion Molecule-1 (VCAM-1), tenascin-C, plasmin, etc. are known. By observing binding inhibition in vitro in the presence of the obtained monoclonal antibody using a cell or a cancer cell in which these ECM and α9 integrin are expressed, a target disease of the monoclonal antibody of the present invention can be found.

In the case of using the anti-human α9 integrin antibody as a medicinal product for treating human, in an in vivo animal model of disease in the stage of preclinical development regarding which effects of the antibody are required to be confirmed, effects of the antibody on the human antigen cannot be confirmed. That is, before a clinical test for confirming therapeutic effects is conducted by administering to human, it is necessary to conduct an animal experiment for confirming therapeutic effects on a target disease. Mouse is preferred as an experimental animal since there are many strains of mouse whose genetic background has been revealed and many models of disease in which almost the same disease as that of human can be observed are known. However, in general, an antibody agent is an antibody to a human antigen, and rarely shows crossreactivity with a corresponding target antigen of mouse. Therefore, by preparing an antibody to the target antigen of mouse and conducting an animal experiment using the same, pharmacological effects of an antibody used in human, estimation of the amount of administration for a clinical test, reactivity to antigens other than the target antigen, development of adverse effects and the like are observed, and thereby action in human can be reflected. Specifically, by administering an anti-mouse α9 integrin antibody to a mouse model of disease, a target disease of the anti-human α9 integrin antibody becomes clear.

[Pharmaceutical Medication Containing Antibody]

A pharmaceutical preparation containing the antibody of the present invention (particularly the monoclonal antibody) as an active component can be used as a therapeutic agent for cancer (e.g., proliferation and metastasis of cancer cells), inflammatory disease (e.g., rheumatoid arthritis, osteoarthritis, hepatitis, bronchial asthma, fibrosis, diabetes, arteriosclerosis, multiple sclerosis, and inflammatory bowel disease (ulcerative colitis, Crohn's disease)), infection disease (e.g., hepatitis), autoimmune disease (e.g., systemic lupus erythematosus, polymyositis, autoimmune thyroid disease, tubulointerstitial nephritis, and myasthenia gravis), bone disease (e.g., osteoporosis) or the like. As used herein, the term "therapeutic" includes the meaning of "prophylactic".

The dose varies depending on a subject to be administered, a target disease, symptoms, a route of administration, etc. For example, in the case of use for prophylaxis and/or therapy of cancer, in general, the antibody of the present invention in an amount of about 0.01 to 20 mg/kg body weight, preferably about 0.1 to 10 mg/kg body weight, and more preferably about 0.1 to 5 mg/kg body weight for a dose is advantageously administered by intravenous injection about 1 to 10 times per month, and preferably about 1 to 5 times per month. An amount conforming thereto can be administered in the case of other parenteral administrations and oral administrations. In the case of particularly severe symptoms, the dose or the number of doses can be increased as needed.

The antibody of the present invention per se can be administered, and further, the antibody in the form of a suitable pharmaceutical composition can also be administered. The pharmaceutical composition to be used for administration comprises: the above-described antibody or a salt thereof; and a pharmacologically acceptable carrier, diluent or excipient. The composition is provided in a formulation suitable for parenteral administration or oral administration.

That is, examples of formulations for parenteral administration include an injection product, a nasal preparation, a suppository and the like, and the injection product includes formulations such as an intravenous injection product, a subcutaneous injection product, an intradermal injection product, an intramuscular injection product, a drip injection product, etc. These injection products can be prepared according to a known method, for example, by dissolving, suspending or emulsifying the above-described antibody or a salt thereof in a sterile aqueous or oily solution generally used for an injection product. Examples of aqueous solutions for injection include saline, an isotonic solution containing glucose, saccharose, mannitol or another adjuvant, etc., and it can be used in combination with a suitable solubilization agent such as alcohol (e.g., ethanol), polyalcohol (e.g., propylene glycol, polyethylene glycol), a nonionic surfactant (e.g., Polysorbate 80, Polysorbate 20, HCO-50 (polyoxyethylene (50 mol) adduct of hydrogenated castor oil)), etc. Examples of oily solutions include sesame oil and soybean oil, and it can be used in combination with a solubilization agent such as benzyl benzoate and benzyl alcohol. The prepared injection solution is generally put into a suitable ampule, vial or syringe. A suppository to be used for rectal administration is prepared by mixing the above-described antibody with a general base for a nasal preparation or a suppository. It is generally considered to be difficult to perform oral administration of protein such as an antibody because of degradation in the digestive system. However, there is a possibility of oral administration depending on application of original ideas to an antibody fragment or a modified antibody fragment and a formulation.

The above-described pharmaceutical composition for parenteral administration is preferably prepared to provide a formulation having an administration unit which is suitable for the administration amount of the active component. Examples of formulations having such an administration unit include an injection product (ampule, vial, and prefilled syringe), a nasal preparation, a suppository and the like. In general, each of the administration units preferably contains the above-described antibody in an amount of 5 to 500 mg, in particular 5 to 100 mg for injection products, and 10 to 250 mg for other formulations.

Each of the aforementioned compositions may contain other active components as long as no undesirable interaction is generated by blending them with the above-described antibody. For example, the pharmaceutical preparation of the present invention may comprise an anti-human α4 integrin antibody in addition to the above-described antibody. The mixing ratio in this case for example, the ratio of anti-human α9 integrin antibody:anti-human α4 integrin antibody can be adjusted within, but not particularly limited to, the range of 1 to 99:99 to 1.

[Diagnostic Agent Comprising the Monoclonal Antibody of the Present Invention]

A pharmaceutical composition comprising the monoclonal antibody of the present invention can be used as a diagnostic agent for inflammatory diseases such as rheumatoid arthritis, hepatitis, bronchial asthma, fibrosis, diabetes, cancer metastasis, arteriosclerosis, multiple sclerosis, granuloma, etc., or a diagnostic agent for autoimmune diseases such as chronic rejection after organ transplantation, systemic autoimmune diseases, erythematosus, uveitis, Behcet's disease, polymyositis, proliferative glomerulonephritis, sarcoidosis, etc. Since the monoclonal antibody of the present invention can specifically recognize α9 integrin, it can be used for quantification of α9 integrin in a test solution, in particular, quantification using sandwich immunoassay, a competition method, an immunometric method, a nephrometry method or the like. When applying each of these immunological measurement methods to the measurement method of the present invention, no particular condition or operation is required. A measurement system for LLPL or a salt thereof can be established by adding a technical arrangement generally considered by those skilled in the art to general conditions and operation methods of each of these methods. Detailed information about these general technical means is described in review articles, authoritative books and so on.

Thus, by using the antibody of the present invention, α9 integrin can be highly-sensitively quantified. Moreover, by utilizing the in vivo quantification method for α9 integrin using the antibody of the present invention, various diseases associated with α9 integrin can be diagnosed. For example, when increase/decrease of the concentration of α9 integrin is detected, it can be diagnosed that there is a high possibility that there is a disease such as inflammatory disease associated with α9 integrin, or that there is a high possibility of being affected with such a disease in future. Moreover, the monoclonal antibody of the present invention can be used in order to specifically detect α9 integrin present in a test analyte such as body fluid and tissue. Furthermore, the monoclonal antibody can be used in preparation of an antibody column to be used for purifying α9 integrin, detection of α9 integrin contained in each fraction over purification, analysis of behavior of α9 integrin in a test cell, etc.

[Method for Screening a Compound which Inhibits Activity of Human α9 Integrin]

A compound which inhibits activity of human α9 integrin can be screened utilizing an epitope on the human α9 integrin recognized by the antibody of the present invention. Specifically, the present invention provides a method for screening a low-molecular compound which inhibits activity of human α9 integrin, wherein a peptide, which comprises one or more amino acid sequences selected from the group consisting of the amino acid sequences set forth in SEQ ID NOs: 1, 2, 3, 4, 5, 6, 7, 8, 9, 10, 11, 12, 13, 14 and 15 (hereinafter referred to as "peptide A"), is used.

The peptide A preferably has at least 2, 3, 4, 5, 6 or 7 amino acid sequences or 8 amino acid sequences selected from the group consisting of the amino acid sequences set forth in SEQ ID NOs: 1, 2, 3, 4, 5, 6, 7, 8, 9, 10, 11, 12, 13, 14 and 15. The peptide A can be synthesized using a known synthesis method. More preferably, the peptide A comprises: (1) the amino acid sequences set forth in SEQ ID NOs: 2, 5, 7, 8, 9, 10, 11 and 12; (2) the amino acid sequences set forth in SEQ ID NOs: 5, 7, 8 and 11; (3) the amino acid sequences set forth in SEQ ID NOs: 2, 3, 5, 8, 9, 11, 12 and 14; (4) the amino acid sequences set forth in SEQ ID NOs: 5, 7, 10, 13 and 14; (5) the amino acid sequences set forth in SEQ ID NOs: 1, 5, 6, 7 and 13; (6) the amino acid sequences set forth in SEQ ID NOs: 10 and 13; or (7) the amino acid sequences set forth in SEQ ID NOs: 5 and 7.

In the screening method of the present invention, for example, comparison between (i) the case in which the peptide A is brought into contact with a ligand of human α9 integrin (e.g., tenascin-C, plasmin, etc.) and (ii) the case in which the peptide A is brought into contact with a ligand and a test compound is carried out. The comparison between the steps (i) and (ii) is carried out, for example, by measuring the binding amount of ligand to the peptide A. In order to facilitate comparison of binding amounts, a ligand labeled according to a known technique is preferably used. A candidate compound obtained in this way is subjected to an experiment to confirm whether or not it inhibits activity of human α9 integrin, and thus a compound which inhibits activity of human α9 integrin is obtained.

As a test substance, a polypeptide, a protein, a nonpeptidic compound from an organism, a synthetic compound, a microbiological culture, a cell extract, a botanical extract, an animal tissue extract, etc. can be used. The test substance can be a novel or known compound.

Like the antibody of the present invention, a selected compound can be used as a prophylactic and/or therapeutic agent for cancer, inflammatory disease, infection disease, autoimmune disease, bone disease, etc.

EXAMPLES

Hereinafter, the present invention will be described in more detail based on Examples, but the present invention is not limited thereto.

Example 1

[Preparation of an Antibody to Human α9 Integrin]

In the preparation of an antibody to human α9 integrin, three BALB/c mice were immunized based on the Subtractive Immunization method (Williams C. V., Stechmann C. L., McLoon S. C., Biotechniques. (1992) 12:842-847). Firstly, CHO-K1 cells ($4\times10^6$) were administered intraperitoneally to each of the mice. On the next day and the following day, cyclophosphamide (4 mg) was administered intraperitoneally to each of the mice. Two weeks after the administration of cyclophosphamide, human α9 integrin-expressing cells (human α9/CHO-K1 cells) ($2\times10^6$) were administered intraperitoneally to each of the mice, and 2 weeks after that, human α9/CHO-K1 cells ($3\times10^6$) were administered intraperitoneally to each of the mice. A clone, which reacted with a human α9/CHO-K1 cell and did not react with a human α4 integrin-expressing CHO-K1 cell, was regarded as an anti-α9 integrin antibody. As a result, 5 hybridoma cell clones (1K11, 21C5, 24I11, 25B6, 28S1) which produce the anti-human α9 integrin antibody were established.

The obtained hybridoma cells 1K11, 21C5, 24I11 and 25B6 and the hybridoma cell 28S1 were deposited to National Institute of Advanced Industrial Science and Technology, International Patent Organism Depositary (Chuo 6, Higashi 1-1-1, Tsukuba-shi, Ibaraki 305-8566) on Feb. 15, 2006 and May 29, 2007, respectively (accession Nos. FERM BP-10510, 10511, 10512 and 10513 and FERM BP-10832).

Example 2

[Epitope Analysis of Anti-Human α9 Integrin Antibody]

Peptides, each of which consists of 12 amino acids obtained by sliding the starting position in human α9 integrin by 3 amino acids in the direction of C-terminus (e.g., peptide consisting of amino acid sequence of positions 1 to 12 from N-terminus, peptide consisting of amino acid sequence of positions 4 to 15 therefrom, peptide consisting of amino acid sequence of positions 7 to 18 therefrom, etc.), were prepared on a cellulose membrane, in which a C6 spacer was disposed, and to which 2 βAla's were bound additionally, to have an amount of 5 nmol/spot. After the membrane was blocked by Blocking buffer (Milk/0.05%, Tween20 in PBS), the membrane was immersed in 10 mL of 1.0 g/mL solution of peroxidase-labeled anti-human α9 integrin antibodies (1K11, 21C5, 24I11 and 25B6) prepared based on the ordinary method at room temperature for 3 hours. The membrane was washed with a wash solution (T-TBS), and then, it was reacted with ECL Detection Reagent at room temperature for 1 minute. Fluorescence produced by enzyme reaction was observed, and epitopes were identified based on fluorescence intensity. As a control, Y9A2, which is a commercially available anti-human α9 integrin antibody, was used.

As shown in Table 1 below, 1K11 recognized positions 79 to 96 (SEQ ID NO: 2), positions 160 to 177 (SEQ ID NO: 5), positions 238 to 252 (SEQ ID NO: 7), positions 277 to 294 (SEQ ID NO: 8), positions 454 to 471 (SEQ ID NO: 10) and positions 556 to 573 (SEQ ID NO: 11) of the amino acid sequence of human α9 integrin (SEQ ID NO: 40); 21C5 recognized positions 79 to 96 (SEQ ID NO: 2), positions 124 to 141 (SEQ ID NO: 3), positions 160 to 177 (SEQ ID NO: 5), positions 238 to 252 (SEQ ID NO: 7), positions 277 to 294 (SEQ ID NO: 8), positions 409 to 432 (SEQ ID NO: 9), positions 454 to 471 (SEQ ID NO: 10), positions 556 to 573 (SEQ ID NO: 11), positions 592 to 621 (SEQ ID NO: 12), positions 706 to 723 (SEQ ID NO: 14) and positions 931 to 951 (SEQ ID NO: 15); 24I1 recognized positions 79 to 96 (SEQ ID NO: 2), positions 142 to 156 (SEQ ID NO: 4), positions 160 to 177 (SEQ ID NO: 5), positions 238 to 252 (SEQ ID NO: 7), positions 277 to 294 (SEQ ID NO: 8), positions 556 to 573 (SEQ ID NO: 11), positions 706 to 723 (SEQ ID NO: 14) and positions 931 to 951 (SEQ ID NO: 15); and 25B6 recognized positions 40 to 51 (SEQ ID NO: 1), positions 160 to 177 (SEQ ID NO: 5), positions 208 to 225

(SEQ ID NO: 6), positions 238 to 252 (SEQ ID NO: 7) and positions 646 to 657 (SEQ ID NO: 13). It was suggested that these antibodies recognize not partial peptides but conformations. The anti-human α9 integrin antibodies obtained in the present invention react with peptides which are different from those reacting with the control Y9A2. Therefore, it can be said that the antibodies recognize epitopes which are different from those recognized by Y9A2.

As shown in FIG. 1, the following matters became clear: in 1K11, CDR of the heavy chain consists of DYNMD (SEQ ID NO: 16), DINPNNGGTIYNQKFQG (SEQ ID NO: 20) and SGVISTDY (SEQ ID NO: 24), and CDR of the light chain consists of RASQEISGYLI (SEQ ID NO: 28), AASTLDS (SEQ ID NO: 32) and YANYPP (SEQ ID NO: 36); in 21C5, CDR of the heavy chain consists of DYYMY (SEQ ID NO: 17), TISDGGNYTYYPDSVKG (SEQ ID NO: 21) and

TABLE 1

Results of epitope mapping

| | 1K11 | 21C5 | 24I11 | 25B6 | Y9A2 |
|---|---|---|---|---|---|
| FQGPADSFFGYA (SEQ ID NO: 1) | − | − | − | ++ | − |
| KSPGAVFKCRVHTNPDRR (SEQ ID NO: 2) | ++ | +++ | ++++ | − | + |
| WMGVSLARQPKADCRVLA (SEQ ID NO: 3) | + | +++ | + | − | + |
| CAHRWKNIYYEADHI (SEQ ID NO: 4) | + | + | +++ | + | + |
| GFCYIIPSNLQAKGRTLI (SEQ ID NO: 5) | +++ | +++++ | +++++ | +++++ | +++++ |
| VMGAPGSFYWAGTIKVLN (SEQ ID NO: 6) | + | + | + | +++ | + |
| VIMNRRYTYLGYAVT (SEQ ID NO: 7) | +++++ | ++ | +++++ | +++++ | +++ |
| VYIFRADRRSGTLIKIFQ (SEQ ID NO: 8) | ++++ | +++++ | +++ | − | + |
| QYSMKLSGQKINPVLRMFGQSISG (SEQ ID NO: 9) | + | ++++ | − | − | + |
| VVLLRARPVITVDVSIFL (SEQ ID NO: 10) | ++ | ++ | − | − | +++++ |
| RHYVAHVKRRVQDVISPI (SEQ ID NO: 11) | +++ | +++ | +++++ | + | ++ |
| ELPPLTPVLWKKGQKIAQKNQTVFERNCR (SEQ ID NO: 12) | + | +++++ | + | − | ++ |
| YLALGAVKNISL (SEQ ID NO: 13) | + | + | − | ++ | +++++ |
| CSVGFPFMRSKSKYEFSV (SEQ ID NO: 14) | + | ++ | ++ | − | +++ |
| SSSVIQFMSRAKVKVDPALRV (SEQ ID NO: 15) | + | ++ | +++ | − | + |

Example 3

[Analysis of Complementarity Determining Region (CDR) of Anti-human α9 Integrin Antibody]

mRNAs were extracted from hybridomas which produce human α9 integrin antibodies (1K11, 21C5, 24I11, 25B6 and 28S1), and cDNAs were prepared by reverse transcription. The cDNAs were used as templates, and PCR was carried out using primers for ScFv cloning (Light Primer Mix, Heavy Primer Mix; Amersham Bioscience). Variable regions of heavy chains and light chains of the antibodies were extended and amplified respectively. Subsequently, each PCR product was incorporated in a pCRII TOPO vector based on the ordinary method. This was sequenced to determine an amino acid sequence. Each of the antibodies was subjected to the above-described operation 3 times.

DRDGSSLFAY (SEQ ID NO: 25), and CDR of the light chain consists of KASQDVNIAVA (SEQ ID NO: 29), WASTRHT (SEQ ID NO: 33) and HYNTPW (SEQ ID NO: 37); in 24I11, CDR of the heavy chain consists of DTYVH (SEQ ID NO: 18), NIDPANGNTKYDPKFQG (SEQ ID NO: 22) and WLRHFYYAMDY (SEQ ID NO: 26), and CDR of the light chain consists of RASENIYYSLA (SEQ ID NO: 30), NANSLED (SEQ ID NO: 34) and AYDVPY (SEQ ID NO: 38); in 25B6, CDR of the heavy chain consists of SYGVH (SEQ ID NO: 19), VIWSGGSTNYNSALMS (SEQ ID NO: 23) and DYGNYPWFAY (SEQ ID NO: 27), and CDR of the light chain consists of KASQDVNTAVA (SEQ ID NO: 31), SASYRYT (SEQ ID NO: 35) and HYSTPC (SEQ ID NO: 39); and in 28S1, CDR of the heavy chain consists of GYGVN (SEQ ID NO: 41), MIWGDGITEYNSALKSR (SEQ ID NO: 42) and DASSGYGFAY (SEQ ID NO: 43), and CDR of the light chain consists of TASSSVSSSYLH (SEQ ID NO: 44), STSNLAS (SEQ ID NO: 45) and YHRSPY (SEQ ID NO: 46).

For the purpose of reference, correspondence between CDRs and SEQ ID NOs is shown in Table 2.

TABLE 2

Correspondence between CDRs and SEQ ID NOs

|       | 1k11 | 21C5 | 24I11 | 25B6 | 28S1 |
|-------|------|------|-------|------|------|
| CDRH1 | 16   | 17   | 18    | 19   | 41   |
| CDRH2 | 20   | 21   | 22    | 23   | 42   |
| CDRH3 | 24   | 25   | 26    | 27   | 43   |
| CDRL1 | 28   | 29   | 30    | 31   | 44   |
| CDRL2 | 32   | 33   | 34    | 35   | 45   |
| CDRL3 | 36   | 37   | 38    | 39   | 46   |

Example 4

[Cell Adhesion Inhibition Effects of Anti-human α9 Integrin Antibody]

Since α9 integrin binds to α9 ligand including an extracellular matrix (ECM) such as OPN, fibronectin, tenascin-C and VCAM-1 at the time of cell adhesion, an extracellular matrix, which may be a target upon inhibiting cell adhesion caused by the obtained anti-human α9 integrin antibody, was examined.

hOPN (RAA)N-half was obtained by the following procedures: GRD sequence in human OPN was converted into RAA sequence; the region from the N-terminus to the thrombin cleavage site was fused to provide GST fusion protein; the GST fusion protein was purified from E. coli; and GST was cleaved and removed using precision protease (Amersham Biosciences). VCAM-1 was obtained from R&D Systems. As tenascin-C, an AEIDGIEL peptide, which is an adhesion sequence region of tenascin-C to α9 integrin, was used. As human fibronectin, a CPEDGIHELFP (SEQ ID NO:49) peptide, which is a partial peptide within EDA region that is important for adhesion to α9 integrin, was synthesized and bound to BSA for use. As a human α9 integrin highly-expressing cell, a CHO-K1 cell expressing human α9 integrin (human α9 /CHO-K1) was used.

1.25 to 5.0 μg/mL of tenascin-C, fibronectin, VCAM-1 or hOPN (RAA)N-half was added to a 96-well plate (50 μl each), and it was allowed to stand at 37° C. for 1 hour to be immobilized. After blocking with a blocking solution (0.5% BSA/PBS), it was washed with PBS once. Human α9/CHO-K1 cell suspended in 0.25% BSA-added D-MEM was mixed with the obtained monoclonal antibody, and 200 μl each was added to reach $1.0 \times 10^5$ cells/ml of the cell number and 10 μg/mL of the antibody concentration. After reaction was performed under 5% $CO_2$ at 37° C. for 1 hour, a solution of 0.5% Crystal Violet (WAKO, Osaka, Japan)/20% methanol was added to wells (50 μl each), and left at room temperature for 30 minutes, and thereby the cells were immobilized and stained. After the plate was washed with distilled water, it was dissolved in 20% acetic acid solution, and absorbance at 590 nm was measured. As a negative control, a monoclonal antibody to human osteopontin (5A1) was used, and as positive control, a commercially available anti-human α9 integrin antibody Y9A2 was used.

Results thereof are shown in FIG. 2. Tenascin-C-associated cell adhesion was inhibited by 21C5, 24I11, 25B6 and 28S1, but not inhibited by 1K11. Fibronectin-associated cell adhesion was inhibited by 21C5, 25B6 and 28S1, slightly inhibited by 24I11 observably, but not inhibited by 1K11. VCAM-1-associated cell adhesion was inhibited by 21C5, 24I11, 25B6 and 28S1 observably, but not inhibited by 1K11. hOPN (RAA)N-half-associated cell adhesion was inhibited by 21C5, 24I11, 25B6 and 28S1, but not inhibited by 1K11.

Example 5

[Cell Adhesion Inhibition Effects Under the Coexistence of Anti-human α4 Integrin Antibody and Anti-human α9 Integrin Antibody]

α4 and α9 integrins bind to many common ECMs. Therefore, it is thought that the presence of antibodies to both the integrins may lead to enhancement of cell adhesion inhibition effects. In order to study in vitro cancer metastasis suppression effects under the coexistence of the anti-human α4 integrin antibody and the anti-human α9 integrin antibody, influence of both the antibodies on adhesion between human melanoma cell (G361), which is a cancer cell expressing α4 integrin and α9 integrin, and ECM was examined.

As ECM, VCAM-1 (1.25 μg/mL) was used, and as an anti-human α4 integrin antibody, P1H4 was used. The examination was carried out in a manner similar to that in Example 4.

Figure 3:
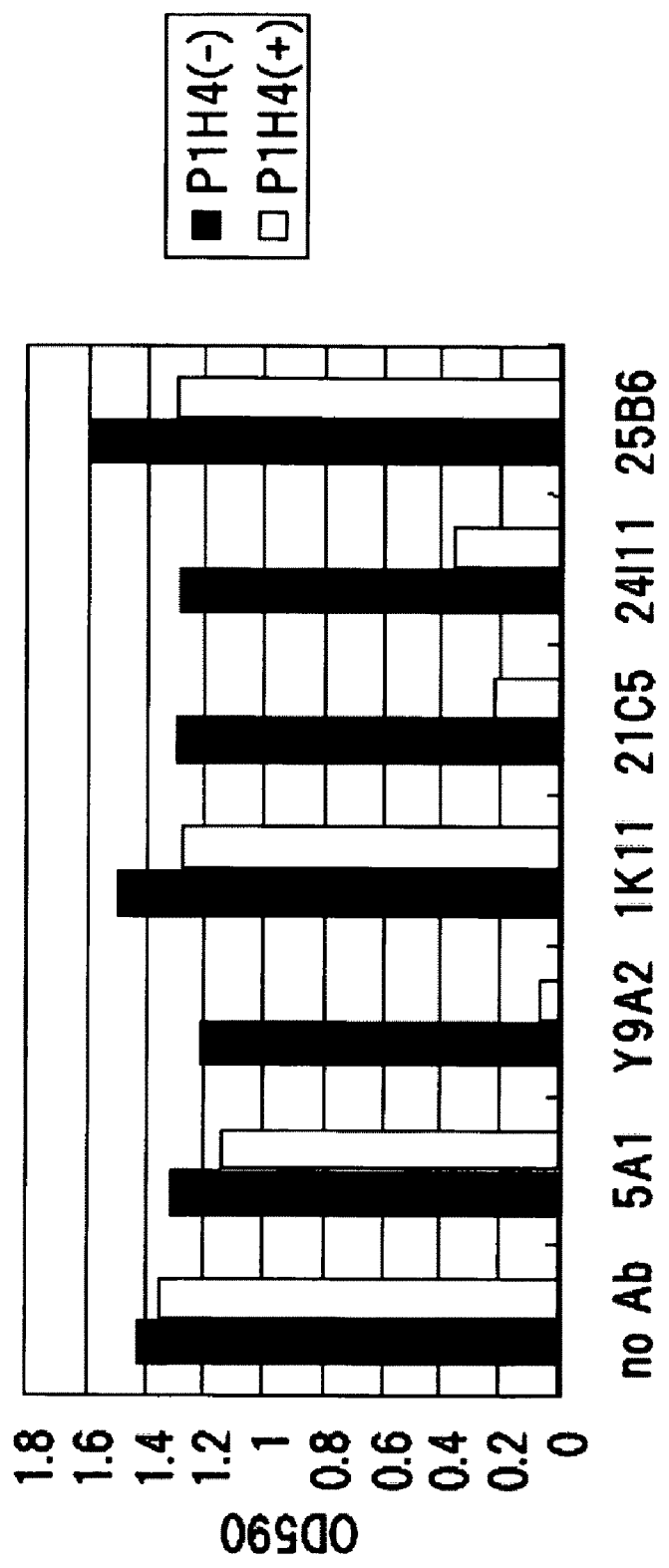
FIG. 3 shows cancer cell (human melanoma cell) adhesion inhibition effects elicited when anti-human α9 integrin antibody and anti-human α4 integrin antibody existed together.

Results are shown in FIG. 3. VCAM-1-associated cell adhesion was not inhibited by all of the antibody. However, under the coexistence of the anti-human α4 integrin antibody, inhibition by positive control (Y9A2), 21C5 and 24I11 was observed. Many cells which expressed α9 integrin also expressed α4 integrin. Therefore, it was suggested that, by using the anti-human α4 integrin antibody and the anti-human α9 integrin antibody in combination, cell adhesion can be suppressed and effects of enhancing suppression against many diseases including cancer invasion can be expected.

Example 6

[Antirheumatic Effects of Anti-mouse α9 Integrin Antibody]

An anti-mouse α9 integrin antibody (55A2C) was administered intraperitoneally to three 7-week-old female mice (Balb/c) (400 μg/mouse), and as control, normal Hamster IgG (hereinafter abbreviated as NHG) was administered intraperitoneally to another three 7-week-old female mice (Balb/c) (400 μg/mouse). 24 hours later, arthritis-causing type II collagen monoclonal antibody cocktail (Chondrex) was administered intravenously (2 mg/mouse). 72 hours after the administration of the type II collagen monoclonal antibody cocktail, 55A2C or NHG was intraperitoneally administered again (400 μg/mouse). At the same time, LPS was administered intraperitoneally (50 μg/mouse). Mice were observed from 3 days before LPS administration to day 6 after LPS administration, and the degree of arthritis was scored based on the method of Wood (F. D. Wood, C. M. Pearson, A Tanaka, Int. Arch. Allergy Appl. Immunol., 35, 456 (1969)).

Figure 4:
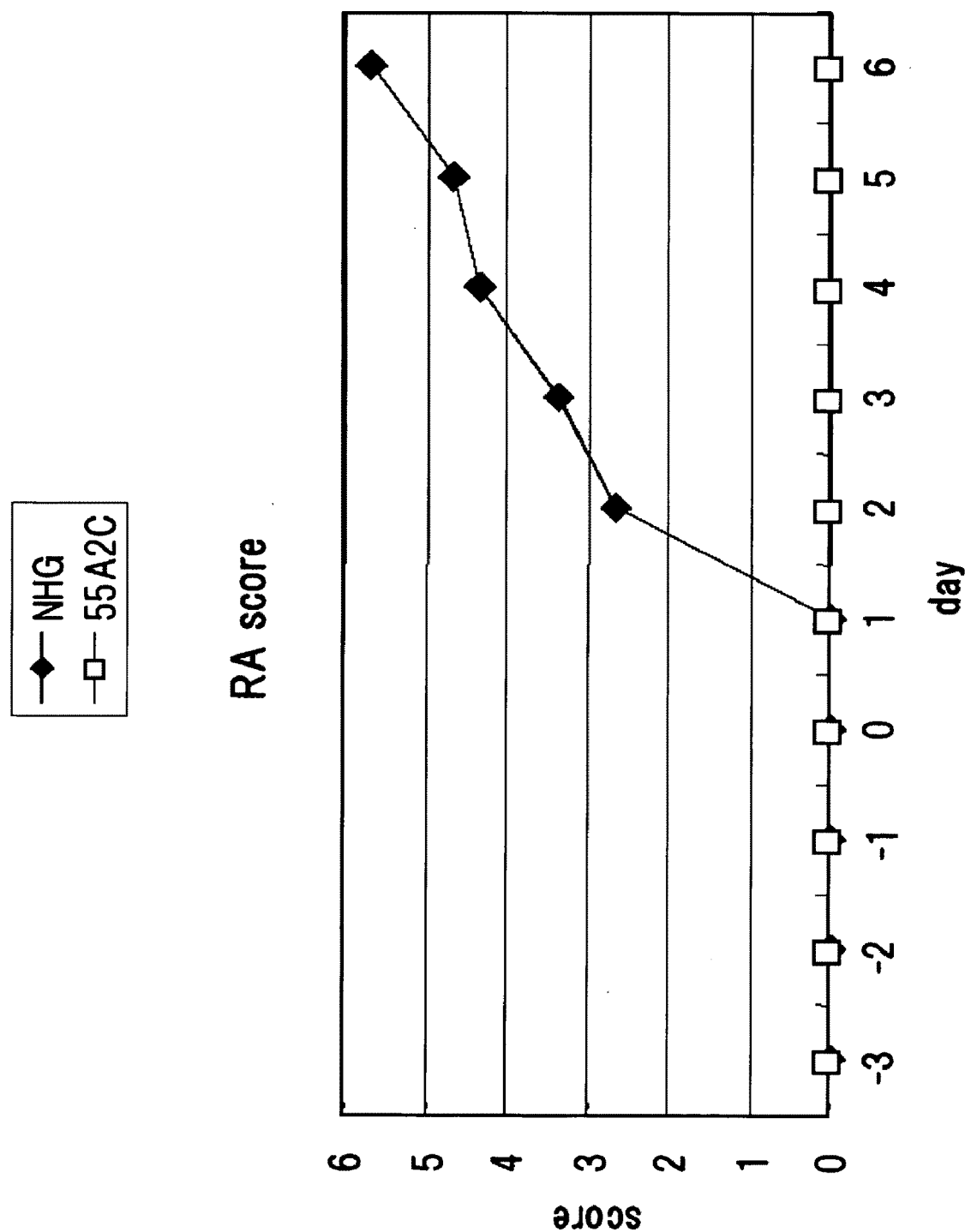
FIG. 4 shows therapeutic effects on rheumatism with anti-mouse α9 integrin antibody in an animal model of rheumatism.

Results are shown in FIG. 4. In the case of control NHG, scores increased and onset of rheumatism was observed. In the case of the anti-mouse α9 integrin antibody, it was suggested that onset of rheumatism is completely suppressed thereby. Therefore, it was understood that the anti α9 integrin antibody has therapeutic effects of suppressing onset or exacerbation of rheumatism.

Example 7

[Therapeutic Effects of Anti-mouse α9 Integrin Antibody on Arthritis]

It has been conventionally thought that helper T cells, which control the immune system, are roughly classified into Th1 and Th2. However, recently, it has become clear that there are also Th17 cells, inhibitory T cells, etc. Further, it was found that only Th17 cells, which are increased by interleukin (IL)-23, have the effect of increasing osteoclasts. Th17 cells produce IL-17 to cause inflammation of surrounding cells, and at the same time, increase osteoclast differentiation factor RANKL (receptor of activator of NF-κB ligand) to generate an environment in which osteoclasts tend to be easily produced. Moreover, it has been reported that, in mice in which genes of Il-23 or IL-17 were disrupted, inflammatory bone destruction did not occur, and that therefore, these factors have an important role in bone destruction. In order to study influence of the anti α9 integrin antibody on Th17, examination was carried out using mouse arthritis model and anti-mouse α9 integrin antibodies.

Anti-mouse α9 integrin antibodies (18R18D, 55A2C) were administered intraperitoneally to three 6-week-old female mice (Balb/c) and another three 6-week-old female mice (Balb/c), respectively (400 μg/mouse). As control, Normal Hamster IgG (hereinafter abbreviated as NHG) was administered intraperitoneally to yet another three 6-week-old female mice (Balb/c) (400 μg/mouse). 18R18D is an anti α9 integrin antibody which does not have ability to suppress cell adhesion. 55A2C is an antibody which has ability to suppress cell adhesion. 24 hours later, arthritis-causing type II collagen monoclonal antibody cocktail (Chondrex) was administered intravenously (2 mg/mouse). 72 hours after the administration of the type II collagen monoclonal antibody cocktail, 55A2C or NHG was intraperitoneally administered again (400 μg/mouse). At the same time, LPS was administered intraperitoneally (50 μg/mouse). Mice were observed from 3 days before LPS administration to day 6 after LPS administration, and the degree of arthritis was scored based on the method of Wood (F. D. Wood, C. M. Pearson, A Tanaka, Int. Arch. Allergy Appl. Immunol., 35, 456 (1969)). That is, evaluation scores are as follows: "0: no symptom, 1: only one small joint such as a finger joint of a limb showed swelling and reddening, 2: two or more small joints or a relatively large joint such as a wrist joint and a ankle joint showed swelling and reddening, 3: one entire limb showed swelling and reddening, and 4: swelling of one more entire limb reaches the maximum level".

Figure 6:
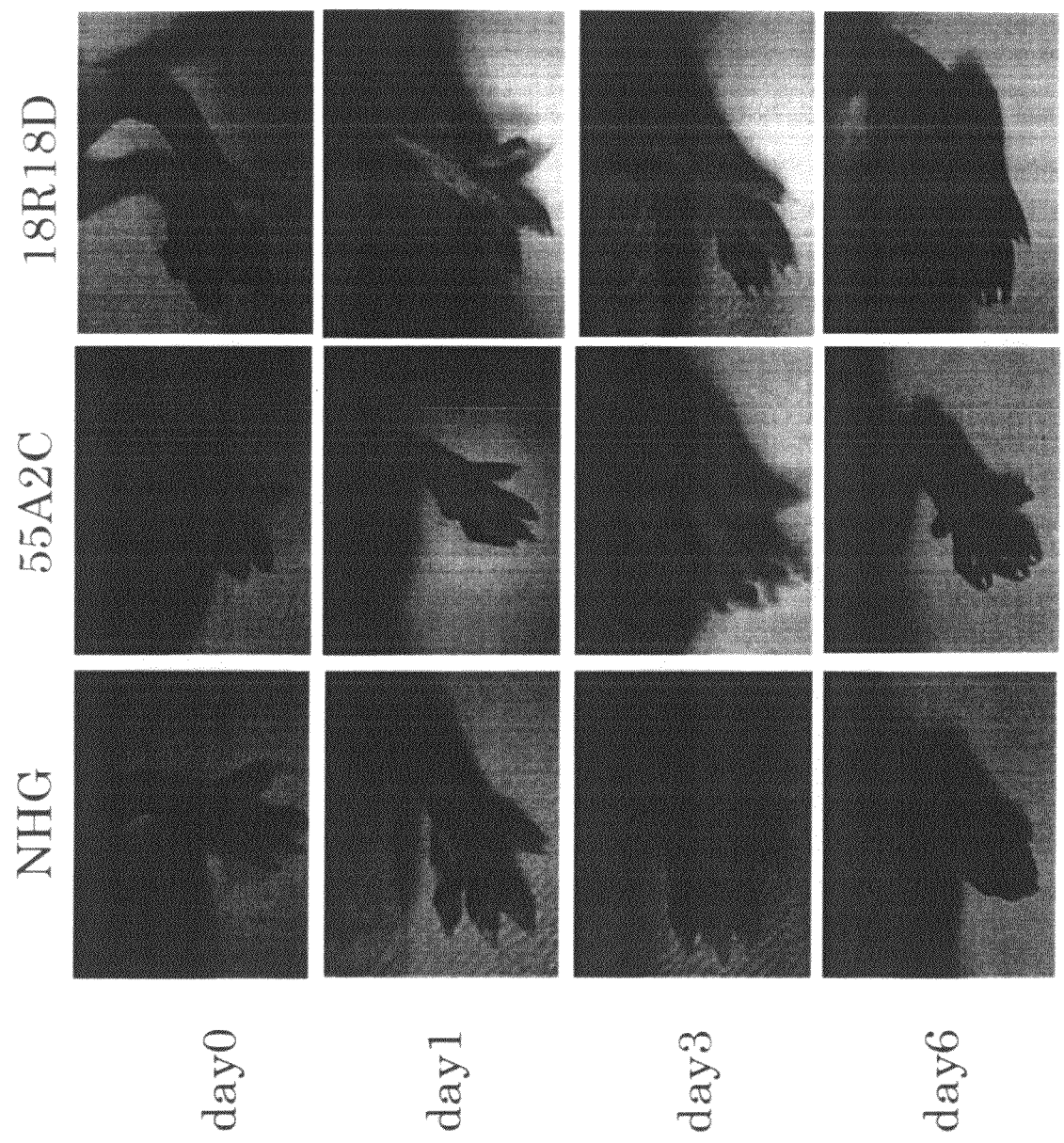
FIG. 6 shows photographs of arthritis suppression attributed to anti-mouse α9 integrin antibody.

Results are shown in FIG. 5. In the case of NHG and 18R18D, scores increased and onset of arthritis was observed. In the case of the anti-mouse α9 integrin antibody 55A2C, it was found that onset of arthritis is dramatically suppressed. It was found that the anti α9 integrin antibody has effects of preventing onset of arthritis as well as effects of suppressing exacerbation thereof. FIG. 6 shows photographs of suppression of arthritis attributed to the anti α9 integrin antibody. It can be understood that swelling of joints was suppressed by 55A2C administration on day 6 after LPS administration.

Next, therapeutic effects of the anti α9 integrin antibody after onset of arthritis were examined. Arthritis-causing type II collagen monoclonal antibody cocktail (Chondrex) was administered intravenously (2 mg/mouse). 72 hours later, LPS was administered intraperitoneally (50 μg/mouse). 3 days later, 55A2C or NHG was administered intraperitoneally (400 μg/mouse), and scoring was conducted. As shown in FIG. 7, it was found that therapeutic effects on arthritis are elicited even when administering the anti α9 integrin antibody after onset of arthritis.

Figure 8:
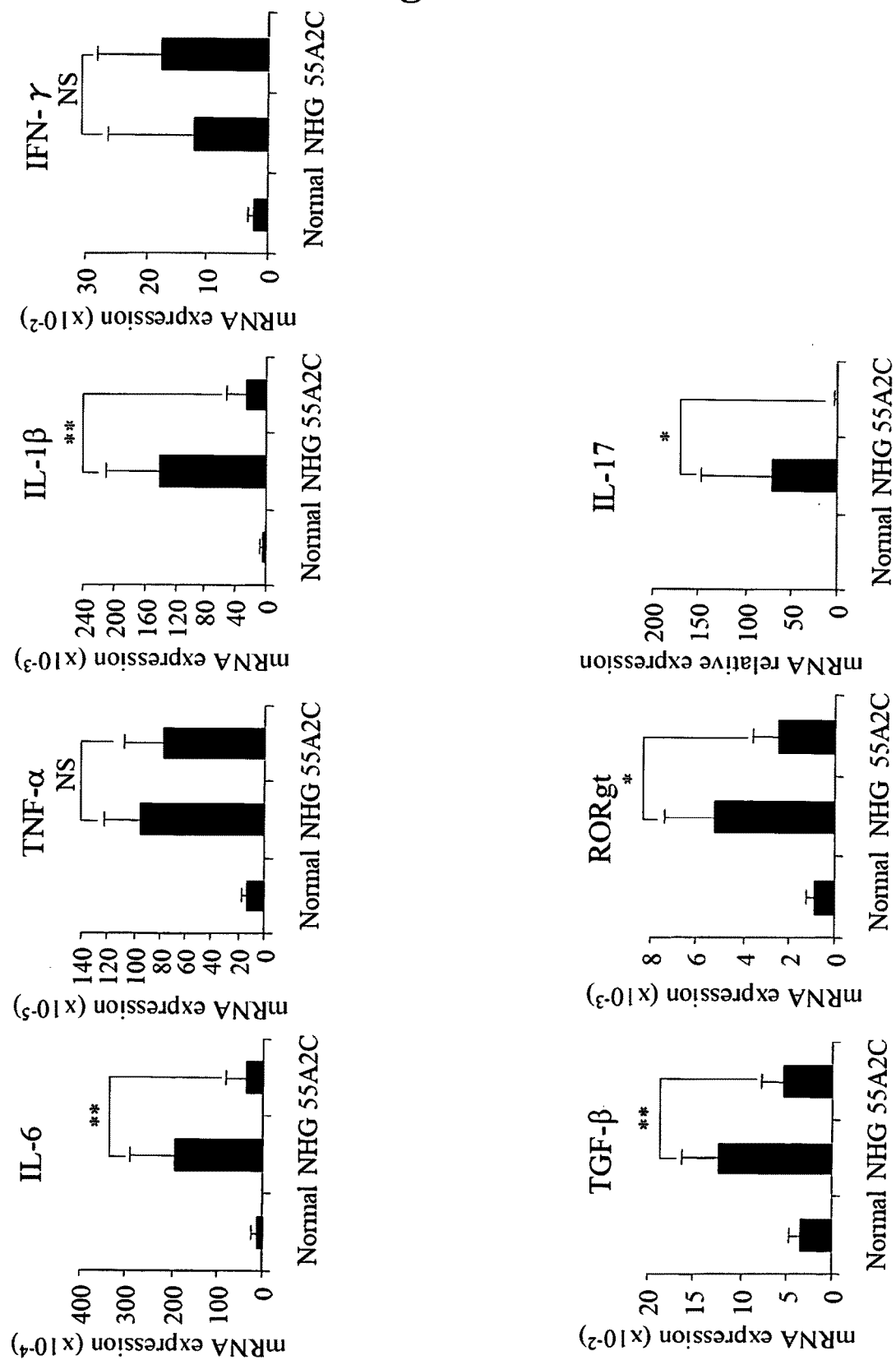
FIG. 8 shows results of examination of change in the amount of cytokine in the joint portion by PCR measurement, which was conducted in order to examine the action mechanism in the therapeutic effects of anti-mouse α9 integrin antibody after the onset of arthritis.

Thus, it was suggested that the anti α9 integrin antibody not only has effects of preventing onset of arthritis but also has therapeutic effects after onset of arthritis. Therefore, the action mechanism thereof was examined. After the anti α9 integrin antibody was administered to a mouse with arthritis, the amounts of change of cytokines (IL-6, TNF-α, IL-1β, IFN-γ and TGF-β) in a lesion of a limb joint were measured by real-time PCR. mRNA expression of IL-6, IL-1β and TGF-α was significantly suppressed in the case of 55A2C-administered group compared to the NHG-administered group (FIG. 8). It has been reported that these cytokines are important for differentiation of Th17. Therefore, it is speculated that the arthritis suppression effects of the anti α9 integrin antibody is attributed to suppression of production of the cytokines that are important for differentiation of Th17, which is caused by inhibition of the α9 integrin function.

Meanwhile, in order to examine involvement of Th17 in the arthritis model, a normal mouse and mice on day 1, day 3 and day 6 after LPS administration (BALB/c, 6-week-old, female) were used, and expression of IL-17 and RORγt (retinoic acid-related orphan receptor γt: a nuclear receptor and transcription factor involved in Th17 differentiation) in inguinal lymph node of each mouse was measured. mRNA expression of IL-17 and RORγt was significantly enhanced with exacerbation of arthritis. Thus, involvement of Th17 in the arthritis model was suggested (FIG. 9). Therefore, in order to examine influence of suppression of the α9 integrin function by the anti α9 integrin antibody on Th17 differentiation, after the anti α9 integrin antibody was administered, expression levels of IL-17 and RORγt in a lesion of a limb joint were measured by real-time PCR. As shown in FIG. 8, expression of the both mRNA was significantly suppressed by the anti α9 integrin antibody. That is, it was understood that the anti α9 integrin antibody suppresses Th17 differentiation.

INDUSTRIAL APPLICABILITY

The antibody of the present invention suppresses the α9 integrin function and thereby elicits therapeutic effects on cancer (e.g., proliferation and metastasis of cancer cells), inflammatory disease (e.g., rheumatoid arthritis, osteoarthritis, hepatitis, bronchial asthma, fibrosis, diabetes, arteriosclerosis, multiple sclerosis, and inflammatory bowel disease (ulcerative colitis, Crohn's disease)), infection disease (e.g., hepatitis), autoimmune disease (e.g., systemic lupus erythematosus, polymyositis, autoimmune thyroid disease, tubulointerstitial nephritis, and myasthenia gravis), bone disease (e.g., osteoporosis) and the like. Additionally, a pharmaceutical composition comprising both the anti-α9 integrin antibody of the present invention and an anti-α4 integrin antibody results in further improved therapeutic effects on cancer, inflammatory disease and the like. The antibody of the present invention can also be utilized as a diagnostic agent since expression of α9 integrin in a cell or tissue can be pathologically detected using the antibody.

The invention claimed is:

1. An isolated anti-human α9 integrin antibody, wherein in the heavy-chain complementarity determining region (CDRH): CDRH1 is the amino acid sequence set forth in SEQ ID NO:16, SEQ ID NO:17, SEQ ID NO:18, SEQ ID NO:19 or SEQ ID NO:41; CDRH2 is the amino acid sequence set forth in SEQ ID NO:20, SEQ ID NO:21, SEQ ID NO:22, SEQ ID NO:23 or SEQ ID NO:42; and CDRH3 is the amino acid sequence set forth in SEQ ID NO:24, SEQ ID NO:25, SEQ ID NO:26, SEQ ID NO:27 or SEQ ID NO:43, and wherein in the light-chain complementarity determining region (CDRL): CDRL1 is the amino acid sequence set forth in SEQ ID NO:28, SEQ ID NO:29, SEQ ID NO:30, SEQ ID NO:31 or SEQ ID NO:44; CDRL2 is the amino acid sequence set forth in SEQ ID NO:32, SEQ ID NO:33, SEQ ID NO:34, SEQ ID NO:35 or SEQ ID NO:45; and CDRL3 is the amino acid sequence set forth in SEQ ID NO:36, SEQ ID NO:37, SEQ ID NO:38, SEQ ID NO:39 or SEQ ID NO:46.

2. The isolated anti-human α9 integrin antibody according to claim 1, which is a monoclonal antibody.

3. The isolated anti-human α9 integrin antibody according to claim 1, which is a chimeric antibody.

4. The isolated anti-human α9 integrin antibody according to claim 1, which is a humanized antibody.

5. An isolated anti-human α9 integrin antibody having all of the complementarity determining regions (CDRs) comprising the amino acid sequence set forth in SEQ ID NO:16, SEQ ID NO:20, SEQ ID NO:24, SEQ ID NO:28, SEQ ID NO:32 and SEQ ID NO:36.

6. An isolated anti-human α9 integrin antibody having all of the complementarity determining regions (CDRs) comprising the amino acid sequence set forth in SEQ ID NO:17, SEQ ID NO:21, SEQ ID NO:25, SEQ ID NO:29, SEQ ID NO:33 and SEQ ID NO:37.

7. An isolated anti-human α9 integrin antibody having all of the complementarity determining regions (CDRs) comprising the amino acid sequence set forth in SEQ ID NO:18, SEQ ID NO:22, SEQ ID NO:26, SEQ ID NO:30, SEQ ID NO:34 and SEQ ID NO:38.

8. An isolated anti-human α9 integrin antibody having all of the complementarity determining regions (CDRs) comprising the amino acid sequence set forth in SEQ ID NO:19, SEQ ID NO:23, SEQ ID NO:27, SEQ ID NO:31, SEQ ID NO:35 and SEQ ID NO:39.

9. An isolated anti-human α9 integrin antibody having all of the complementarity determining regions (CDRs) comprising the amino acid sequence set forth in SEQ ID NO:41, SEQ ID NO:42, SEQ ID NO:43, SEQ ID NO:44, SEQ ID NO:45 and SEQ ID NO:46.

10. An isolated anti-human α9 integrin antibody produced by a hybridoma cell having accession No. FERM BP-10510, FERM BP-10511, FERM BP-10512, FERM BP-10513 or FERM BP-10832.

* * * * *